(12) United States Patent
Edwards et al.

(10) Patent No.: US 8,152,807 B2
(45) Date of Patent: Apr. 10, 2012

(54) INTRAMEDULLARY DEVICE ASSEMBLY AND ASSOCIATED METHOD

(75) Inventors: Scott G. Edwards, McLean, VA (US); Ronald Arthur Yapp, Manchester, MI (US)

(73) Assignee: Olecranail LLC, McLean, VA (US)

( * ) Notice: Subject to any disclaimer, the term of this patent is extended or adjusted under 35 U.S.C. 154(b) by 641 days.

(21) Appl. No.: 12/059,701

(22) Filed: Mar. 31, 2008

(65) Prior Publication Data
US 2009/0248024 A1 Oct. 1, 2009

(51) Int. Cl.
*A61B 17/56* (2006.01)
*A61B 17/58* (2006.01)
*A61F 2/30* (2006.01)

(52) U.S. Cl. ........................................................ 606/62

(58) Field of Classification Search .............. 606/62–64, 606/87, 89, 92–100
See application file for complete search history.

(56) References Cited

U.S. PATENT DOCUMENTS

| | | | |
|---|---|---|---|
| 3,858,866 A * | 1/1975 | Armstrong et al. ............. | 269/46 |
| 4,091,806 A | 5/1978 | Aginsky | |
| 4,103,683 A | 8/1978 | Neufeld | |
| 4,875,474 A | 10/1989 | Border | |
| 4,911,153 A | 3/1990 | Border | |
| 4,981,481 A | 1/1991 | Kranz et al. | |
| 5,013,317 A | 5/1991 | Cole et al. | |
| 5,030,222 A | 7/1991 | Calandruccio | |
| 5,057,110 A | 10/1991 | Kranz et al. | |
| 5,100,404 A | 3/1992 | Hayes | |
| 5,108,398 A | 4/1992 | McQueen et al. | |

(Continued)

FOREIGN PATENT DOCUMENTS
DE 28 30 566 1/1980
(Continued)

OTHER PUBLICATIONS
*S.S.T® Small Bone Locking Nail; Forearm Nail; Surgical Technique*; BIOMET INC.; 1998; 24 pages.
(Continued)

*Primary Examiner* — Eduardo C Robert
*Assistant Examiner* — Nicholas Plionis
(74) *Attorney, Agent, or Firm* — Alston & Bird LLP

(57) ABSTRACT

An intramedullary device assembly is provided for repairing defects of a bone. The intramedullary device assembly includes a device that is configured to be inserted into the medullary canal of the bone. The assembly also includes a guide adapter that attaches to the end of the device and includes a movable and adjustable bone engagement member. Also a compression member may be attached to the guide adapter that pushes the bone engagement member into engagement with the bone. The bone engagement member defines at least two bone engagement points and wherein at least one bone engagement point is movable relative to at least one other bone engagement point in the direction of the bone. The compression member forces the bone engagement member in the direction of the bone along the bone engagement member guide and the at least one bone engagement point is permitted to move relative to the other at least one bone engagement point so that both bone engagement points can engage the end of the bone as compression is applied to the bone. The guide adapter and compression member may then be detached from the intramedullary device. A breakaway stud may also be included to connect the guide adapter to the intramedullary device such that the application of force on the assembly may break the breakaway stud and detach the guide adapter and compression member from the installed intramedullary device.

40 Claims, 15 Drawing Sheets

U.S. PATENT DOCUMENTS

| | | | |
|---|---|---|---|
| 5,207,753 A | 5/1993 | Badrinath | |
| 5,219,174 A | 6/1993 | Zurbrugg et al. | |
| 5,284,313 A | 2/1994 | Hallgren | |
| 5,352,228 A | 10/1994 | Kummer | |
| 5,472,444 A | 12/1995 | Huebner et al. | |
| 5,484,446 A | 1/1996 | Burke et al. | |
| 5,569,262 A * | 10/1996 | Carney | 606/96 |
| 5,665,086 A | 9/1997 | Itoman et al. | |
| 5,766,174 A | 6/1998 | Perry | |
| 5,779,705 A | 7/1998 | Matthews | |
| 5,910,143 A | 6/1999 | Cripe et al. | |
| 5,951,561 A | 9/1999 | Pepper et al. | |
| 6,001,104 A | 12/1999 | Benderev et al. | |
| 6,039,742 A | 3/2000 | Krettek et al. | |
| 6,120,504 A | 9/2000 | Brumback et al. | |
| 6,183,477 B1 | 2/2001 | Pepper | |
| 6,270,499 B1 * | 8/2001 | Leu et al. | 606/64 |
| 6,379,360 B1 | 4/2002 | Ackeret et al. | |
| 6,402,766 B2 * | 6/2002 | Bowman et al. | 606/151 |
| 6,443,954 B1 | 9/2002 | Bramlet et al. | |
| 6,569,165 B2 | 5/2003 | Wahl et al. | |
| 6,783,529 B2 | 8/2004 | Hover et al. | |
| 6,786,908 B2 | 9/2004 | Hover et al. | |
| 6,808,527 B2 | 10/2004 | Lower et al. | |
| 6,932,819 B2 | 8/2005 | Wahl et al. | |
| 7,033,363 B2 | 4/2006 | Powell | |
| 7,056,322 B2 | 6/2006 | Davison et al. | |
| 7,066,943 B2 | 6/2006 | Zirkle, Jr. | |
| 2003/0004513 A1 * | 1/2003 | Guzman et al. | 606/62 |
| 2005/0049592 A1 * | 3/2005 | Keith et al. | 606/61 |
| 2005/0107794 A1 * | 5/2005 | Hazebrouck | 606/62 |
| 2006/0015101 A1 * | 1/2006 | Warburton et al. | 606/62 |
| 2006/0142778 A1 | 6/2006 | Dees, Jr. | |
| 2007/0100343 A1 | 5/2007 | Cole et al. | |
| 2007/0276382 A1 | 11/2007 | Mikhail et al. | |
| 2008/0147066 A1 | 6/2008 | Longsworth et al. | |
| 2008/0264109 A1 | 10/2008 | Ritchey et al. | |
| 2008/0269744 A1 | 10/2008 | Kay et al. | |

FOREIGN PATENT DOCUMENTS

| | | |
|---|---|---|
| EP | 0 923 906 A2 | 6/1999 |
| GB | 2 423 021 A | 8/2006 |
| WO | WO 03/059181 A1 | 7/2003 |

OTHER PUBLICATIONS

*S.S.T® Small Bone Locking Nail; Forearm Nail; Surgical Technique*; BIOMET INC.; 1998; 12 pages.

Dragovich, Steve; *SPC, FMEA—When it Comes to Titanium Implants, it Doesn't Mean a Thing Unless the Deburring is Controlled*; Implant Manufacturing; BONEZone; Fall 2003; pp. 9-10.

Technique Guide; *The Olecranon Osteotomy Nailing System*; Synthes; Nov. 8, 2007 5:02 PM; 21 pages.

Knowles Pins from DePuy Orthopaedics, Inc.; *Medcompare™ The Buyer's Guide for Medical Professionals*; 3 pages; located at http://www.medcompare.com/details/34185/Knowles-Pins.html.

Partial International Search Report attached to Invitation to Pay Additional Fees and, Where Applicable, Protest Fee mailed Nov. 6, 2009 and issued in connection with International Application No. PCT/US2008/060294.

*Ankle Arthrodesis Nail—Surgical Technique*; 2000; 20 pages; Biomet Inc.; available at <http://ww.biomet.co.uk/medhome-uk/trauma/internal-fixation/ankle-arthodesis-nail> (visited Sep. 29, 2008).

George E. Quill, Jr. M.D.; *The Use of a Second Generation Intramedullary Nail in Fixation of Difficult Ankle and Hindfoot Arthrodeses*;10 pages; available at <http://www.louortho.com/documents> (visited Sep. 29, 2008).

* cited by examiner

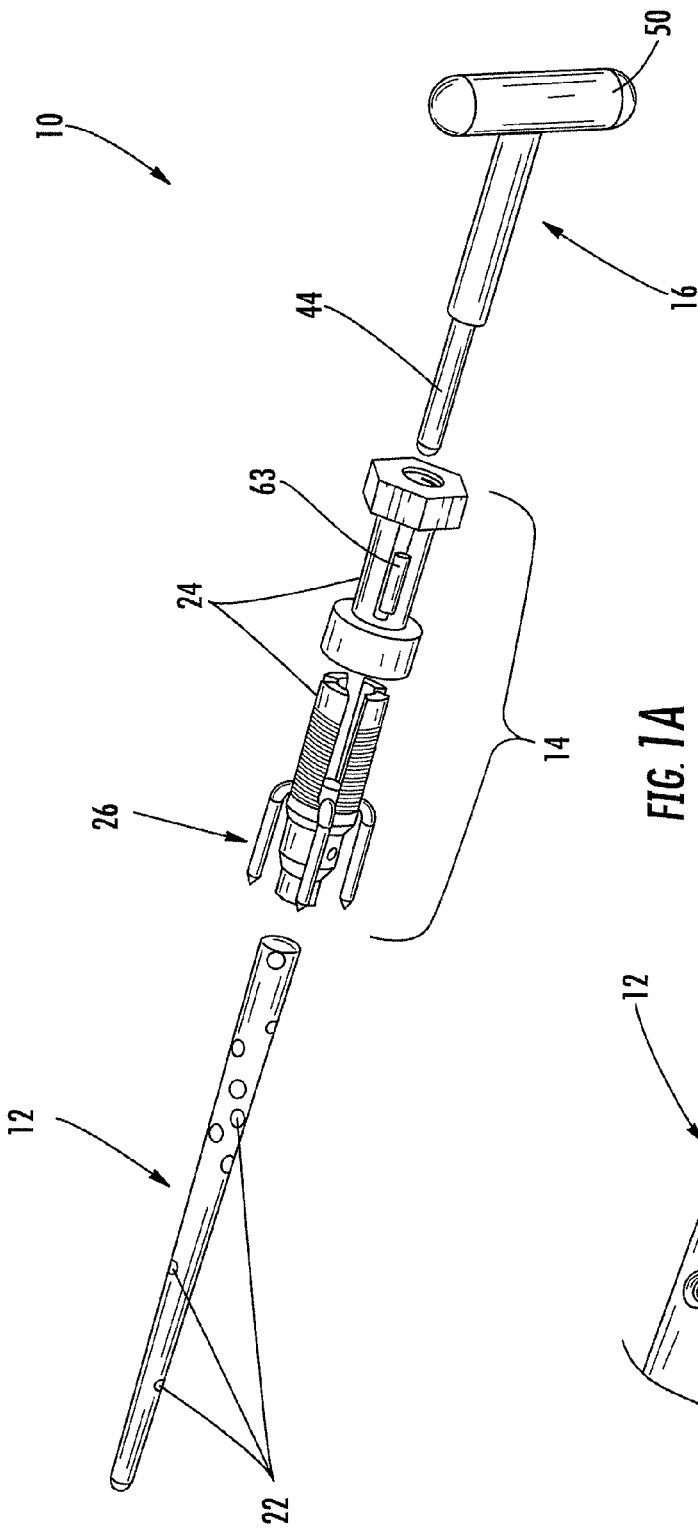

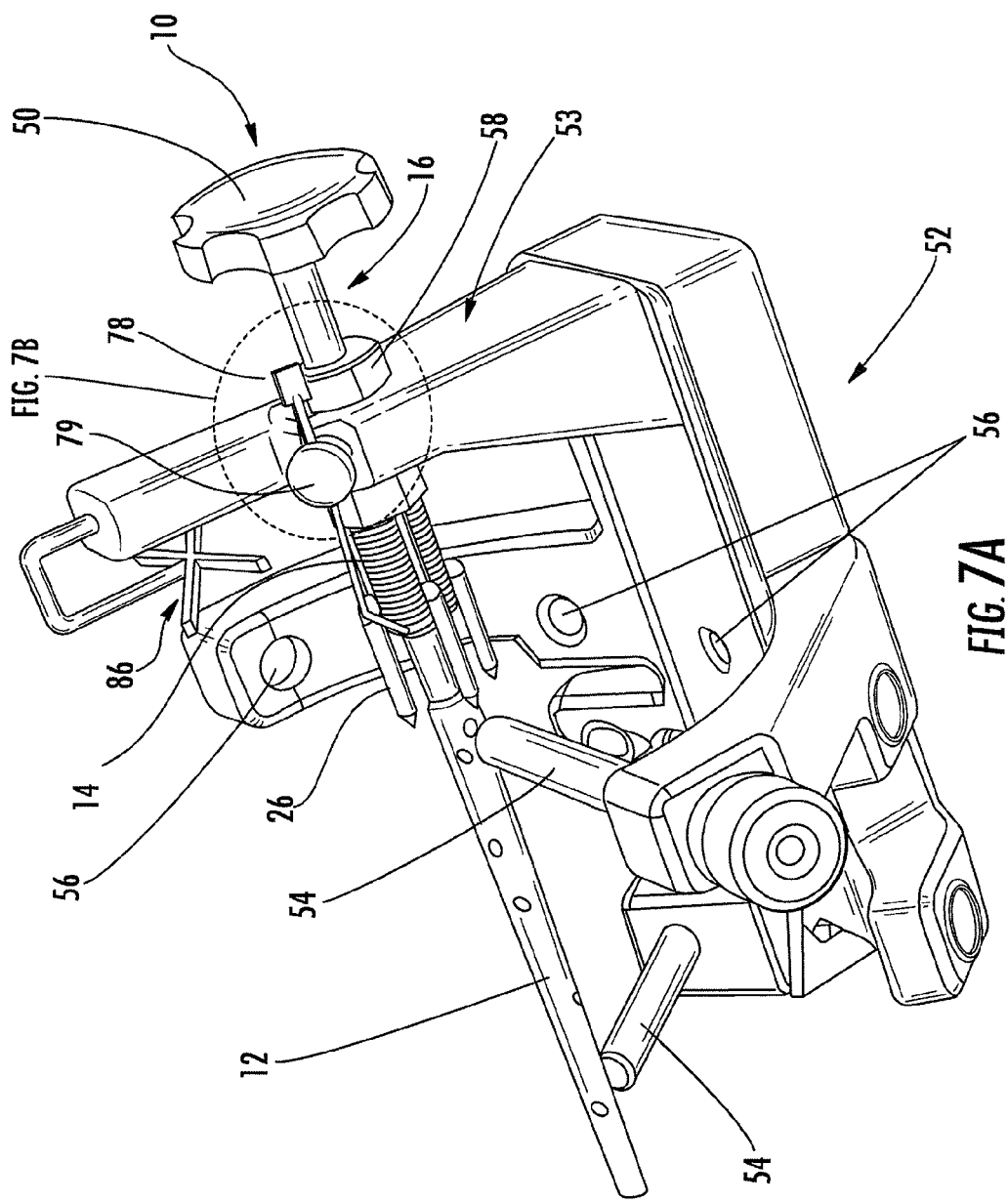

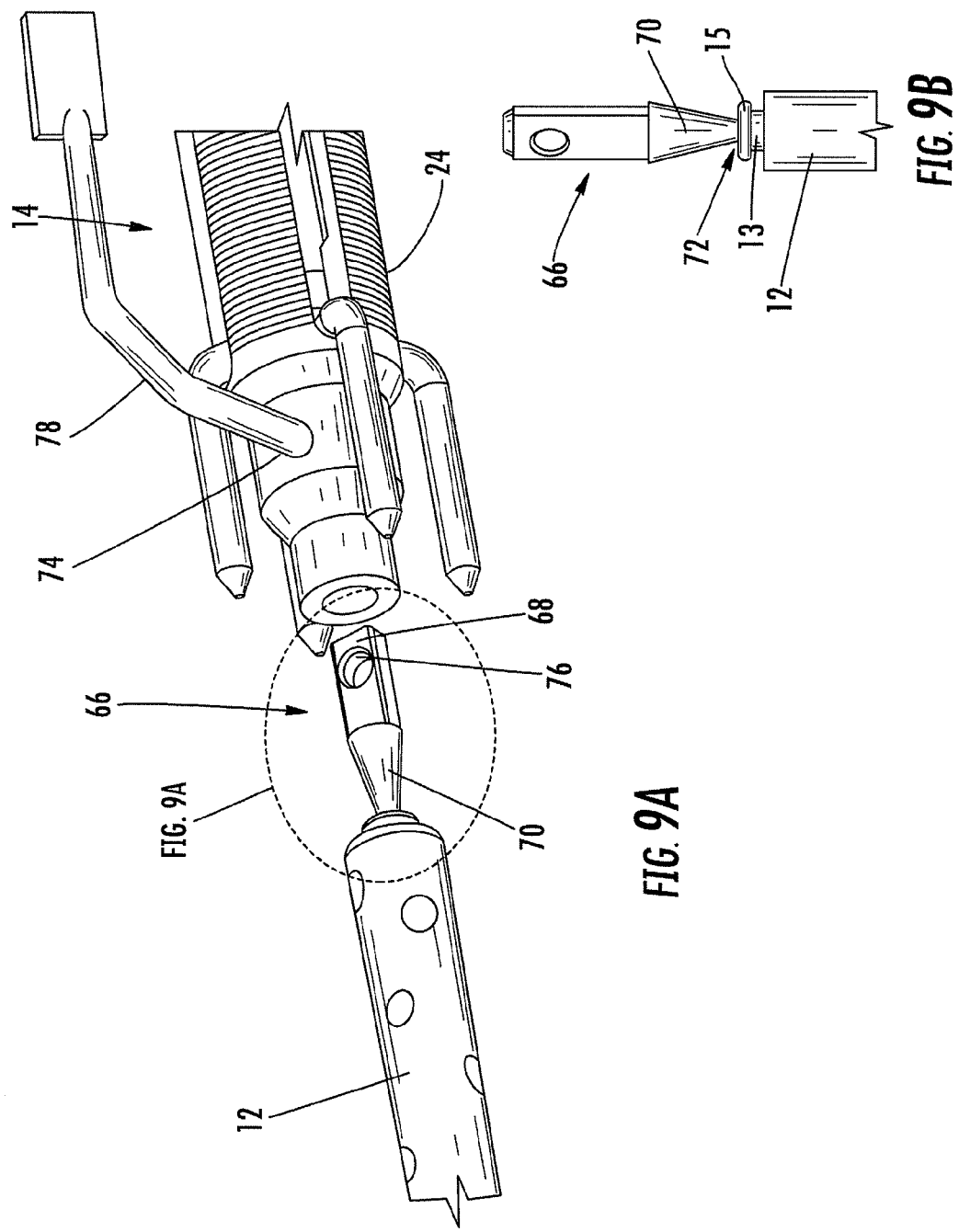

INTRAMEDULLARY DEVICE ASSEMBLY AND ASSOCIATED METHOD

FIELD OF THE INVENTION

The present invention relates to intramedullary devices for repairing bone defects and, more specifically, to intramedullary device assemblies for providing fixation, compression, and/or stabilization of the diaphysis or metaphysis of a long bone or periarticular bone.

BACKGROUND OF THE INVENTION

Intramedullary devices, such as nails, rods, or pins, are often used in the medical field to treat fractures of long bones, such as in the ulna and femur. These intramedullary devices also may be used to treat periarticular fractures, such as in the distal radius and proximal humerus. Such devices are typically designed to be inserted into the medullary canal of the fractured bone and generally are fastened to the bone segments on either side of the fracture to stabilize the bone and promote proper healing.

In some cases, the bone segments on either side of a fracture are spaced apart and must be brought closer together at the fracture to promote healing. Devices have been proposed that provide compression to such bone fractures by fixing the intramedullary device to one bone segment and then moving the free bone segment towards the fixed bone segment by way of compression applied to the end of the free bone segment. The free bone segment is then secured to the intramedullary device and the fracture is allowed to heal. However, these devices may not engage the end of the free bone segment in a manner that takes into account the bone structure at the end of the bone segment or provide balanced compression.

The structure of some bones, such as the ulna and femur, include a relatively hard outer shell comprised of cortical bone, and a relatively softer portion within the shell comprised of cancellous bone. In certain portions of bone, such as periarticular areas, the cortical bone can become quite thin and brittle. Thus, care must be taken when applying a compressive force to the end of the bone not to fracture or damage the cortical bone. Applying the compressive force in an unbalanced fashion to the end of the bone can be damaging to the cortical bone and may not provide a balanced compressive force at the fracture site.

Thus, there remains a need for an intramedullary device assembly that is easy to install without the need for extensive surgical dissection, and provides appropriate and balanced compression of the bone to promote healing.

BRIEF SUMMARY OF THE INVENTION

The present invention generally relates to an intramedullary device assembly for applying and maintaining compression of a bone. Advantageously, in one embodiment, the intramedullary device assembly includes a bone engagement member that is movable along a bone engagement member guide and includes bone engagement points where at least one of the bone engagement points is movable along an axis of the bone engagement member guide relative to another bone engagement point. The bone engagement member may be advanced along the bone engagement member guide by a compression member of the assembly and, in one exemplary embodiment, the bone engagement member can tilt to engage the end of the bone. Thus, the intramedullary device assembly may be easily inserted into the medullary canal of the bone at a joint, such as at the olecranon or the ankle malleolus, and is configured to provide appropriate and balanced compression of the bone to promote healing.

In one embodiment, the intramedullary device assembly includes an intramedullary device, a bone engagement member guide, a compression member, and a bone engagement member. The intramedullary device is configured to be inserted into the medullary canal of the bone and fastened to the bone on either side of the defect. The bone engagement member guide is configured to attach to an end of the intramedullary device, and the compression member is movable along the bone engagement member guide. The bone engagement member, which is also movable along the bone engagement member guide, includes at least two bone engagement points, where at least one bone engagement point is movable along an axis of the bone engagement member guide relative to at least one other bone engagement point and is configured to engage an end of the bone. Thus, application of force on the bone engagement member by the compression member in the direction of the bone advances the bone engagement member along the bone engagement member guide such that the at least one bone engagement point of the bone engagement member is permitted to move relative to the other at least one bone engagement point so that both bone engagement points can securely engage the end of the bone.

In some embodiments, the bone engagement member guide defines an elongated void, and the bone engagement member includes an internal part and an external part. The internal part is configured to be movably retained within the bone engagement member guide, and the external part is configured to extend outside of the bone engagement member guide and engage the end of the bone via at least one of the bone engagement points. The compression member may be configured to apply force to the internal part of the bone engagement member, and the external part of the bone engagement member may include one or more pressing elements configured to engage the end of the bone. The external part of the bone engagement member may, in some cases, include at least two pressing elements, and at least one of the pressing elements may be shorter than the other pressing elements.

The bone engagement member of the intramedullary device assembly may, in some cases, be configured to attach to a drill guide. The bone engagement member may define a keyway slot configured to permit alignment of the drill guide with respect to the intramedullary device assembly.

In some embodiments, the intramedullary device assembly may include a breakaway stud connecting the intramedullary device and the bone engagement member guide. The breakaway stud is configured to break away from the intramedullary device when a predetermined amount of force is applied to the breakaway stud. In some cases, this breakaway action may occur after the bone engagement member guide and the compression member have been detached from the intramedullary device. The breakaway stud may also be configured to fit in a corresponding recess in the bone engagement member guide to limit rotation of the bone engagement member guide with respect to the intramedullary device. The bone engagement member guide may further define a transverse locking hole, and the breakaway stud may define a corresponding transverse locking hole, where the locking holes are configured to receive a locking mechanism such that the bone engagement member guide and the breakaway stud are locked together when the locking mechanism is in place. Furthermore, the intramedullary device may define a nub having a circumferential lip configured to at least partially engage the bone engagement member guide.

In another embodiment, the intramedullary device assembly includes an intramedullary device configured to be inserted into the medullary canal of the bone and fastened to the bone on either side of the defect, a bone engagement member guide, a compression member, and a bone engagement member. The bone engagement member guide is configured to attach to the end of the intramedullary device, and the compression member is movable along the bone engagement member guide. The bone engagement member of this embodiment includes a number of discrete pressing elements configured to engage an end of the bone. The bone engagement member is movable along the bone engagement member guide, and application of force on the bone engagement member by the compression member in the direction of the bone advances the bone engagement member along the bone engagement member guide towards the intramedullary device and allows at least one of the pressing elements to engage the end of the bone. The bone engagement member guide may include a tab configured to fit in a corresponding notch in the intramedullary device to limit rotation of the bone engagement member guide with respect to the device.

The intramedullary device assembly may include a breakaway stud connecting the intramedullary device and the bone engagement member guide. The breakaway stud is configured to break away from the intramedullary device when a predetermined amount of force is applied to the breakaway stud. In some cases, the break away action may occur after the bone engagement member guide and the compression member have been detached from the intramedullary device. The bone engagement member guide may define a transverse locking hole, and the breakaway stud may define a corresponding transverse locking hole, where the locking holes are configured to receive a locking mechanism such that the bone engagement member guide and the breakaway stud are locked together when the locking mechanism is in place. The intramedullary device assembly may further define a nub having a circumferential lip configured to at least partially engage the bone engagement member guide.

In some embodiments, a guide adapter for attaching a compression member and drill guide to an intramedullary device is provided. The guide adapter includes a bone engagement member guide and a bone engagement member movable along the bone engagement member guide. One end of the bone engagement member guide includes a tab configured to engage the intramedullary device and limit rotation of the guide adapter with respect to the device, and another end of the bone engagement member guide is configured to support the compression member. The bone engagement member includes at least two bone engagement points, where at least one of the bone engagement points is movable along an axis of the bone engagement member guide relative to at least one other bone engagement point and is configured to engage an end of a bone when the intramedullary device is installed.

In some cases, the bone engagement member guide defines an elongated void, and the bone engagement member includes an internal part and an external part. The internal part is configured to be movably retained within the bone engagement member guide, and the external part is configured to extend outside of the bone engagement member guide and engage the end of the bone via at least one of the bone engagement points. The external part of the bone engagement member may include a number of pressing elements configured to engage the end of the bone, and at least one of the pressing elements may be shorter than the other pressing elements. Furthermore, the bone engagement member guide may define a keyway slot configured to permit alignment of the drill guide with respect to the guide adapter when the drill guide is attached to the guide adapter. In some embodiments, one end of the guide adapter is configured to attach to a breakaway stud connecting the guide adapter to the intramedullary device.

In other embodiments, a method of assembling an intramedullary device assembly for repairing a bone defect is provided. A guide adapter is attached to a proximal end of an intramedullary device, where the guide adapter includes a bone engagement member guide and a bone engagement member movable along the bone engagement member guide. The bone engagement member guide has a first end configured to attach to the proximal end of the intramedullary device, and the bone engagement member includes at least two bone engagement points. At least one bone engagement point is movable along an axis of the bone engagement member guide relative to at least one other bone engagement point and is configured to engage an end of the bone. The method further includes attaching a compression member to a second end of the bone engagement member guide, where the compression member is movable along the bone engagement member guide.

A drill guide may also be attached to the guide adapter, where the drill guide is configured to allow drilling holes through the bone that are in alignment with corresponding holes defined by the intramedullary device. Furthermore, attaching the guide adapter to the proximal end of the intramedullary device may include providing a breakaway stud at the proximal end of the intramedullary device and attaching the first end of the bone engagement member guide to the breakaway stud. In some cases, the guide adapter may be engaged with a lip formed on a nub defined by the proximal end of the intramedullary device. A locking mechanism may also be inserted through corresponding transverse locking holes formed in the guide adapter and the breakaway stud.

In other embodiments, a method of applying compression to repair a defect of a bone using an intramedullary device assembly including an intramedullary device, a bone engagement member guide attached to the intramedullary device, a bone engagement member movable along the bone engagement member guide, and a compression member is provided. The intramedullary device of the intramedullary device assembly is inserted into the medullary canal of the bone, and the intramedullary device is fastened to a distal segment of the bone located on a distal side of the defect. The compression member is advanced towards the bone and into engagement with the bone engagement member of the intramedullary device assembly. The bone engagement member includes at least two bone engagement points, and at least one bone engagement point is movable along an axis of the bone engagement member guide relative to at least one other bone engagement point and is configured to engage the end of the bone. The bone engagement member continues to advance with the compression member such that the distal segment of the bone is moved towards a proximal segment of the bone located on a proximal side of the defect. Furthermore, the intramedullary device is fastened to the proximal segment to maintain compression of the distal and proximal segments of the bone.

In some cases, the bone engagement member guide and the compression member may be detached from the inserted and fastened intramedullary device. The method may include detaching the bone engagement member guide and the compression member from the intramedullary device by disconnecting the breakaway stud from the bone engagement member guide and subsequently separating the breakaway stud from the intramedullary device.

In other embodiments, an intramedullary device and breakaway stud for attaching an intramedullary device to a bone engagement member guide are provided. The intramedullary device is configured to be inserted into the medullary canal of a bone and fastened to the bone on either side of a defect. The breakaway stud includes a proximal portion and a distal portion, where the proximal portion is configured to engage the bone engagement member guide and the distal portion is configured to engage the intramedullary device. The distal portion includes a region of concentrated stress such that force applied to the breakaway stud is focused in the region of concentrated stress and causes the breakaway stud to break at or near the region of concentrated stress, thereby detaching the breakaway stud from the intramedullary device.

In some cases, the proximal portion of the breakaway stud is domino-shaped, and the distal portion of the breakaway stud may be tapered. Furthermore, the region of concentrated stress of the distal portion of the breakaway stud may be a region having a cross-sectional area that is smaller than other cross-sectional areas of the breakaway stud.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1A is an expanded perspective view of an intramedullary device assembly according to one embodiment;

FIG. 1B is an illustration of an intramedullary device with chamfered hole openings according to one embodiment;

FIG. 7A is a perspective view of an intramedullary device assembly with attached drill guide according to one embodiment;

FIG. 9A is a close-up perspective view of the breakaway stud of FIG. 8;

FIG. 9B is a side plan view of the breakaway stud of FIG. 9A;

DETAILED DESCRIPTION OF THE DRAWINGS

Figure 2A:
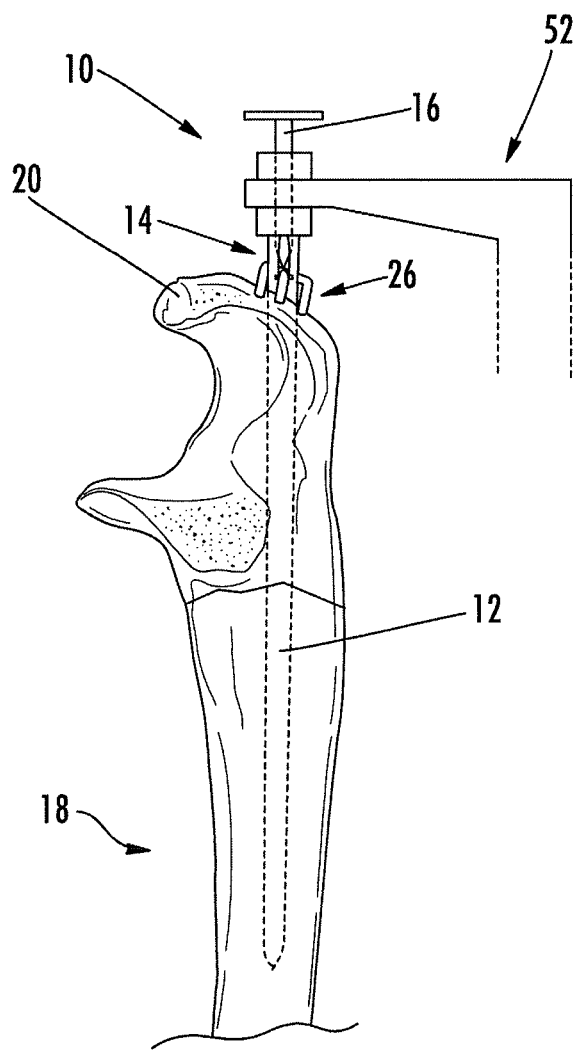
FIG. 2A is an illustration of an intramedullary device assembly installed in an ulna according to one embodiment.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention generally relate to an intramedullary device assembly for repairing fractures, osteotomies, and other defects of a long bone or periarticular bone. For ease of explanation, however, the specification and accompanying figures will refer to bone fractures, although it is to be understood that any type of bone repair, including the repair of fractures, osteotomies, and other bone defects, and combinations thereof, may be accomplished using embodiments of the device described herein.

As described further below, the intramedullary device assembly includes a device that is configured to be inserted into the medullary canal of the fractured bone. A guide adapter attaches to the end of the intramedullary device and includes a movable bone engagement member configured such that a compression member attached to the guide adapter at an opposite end from the device can push the bone engagement member to engage the end of the bone. By fastening the installed intramedullary device to the bone segment on a distal side of the fracture and then applying compression via the compression member and bone engagement member, the fastened bone segment may be pushed towards the bone segment on the proximal side of the fracture. Once the desired compression is achieved, the proximal bone segment may be fastened to the intramedullary device, and the guide adapter and compression member may be detached from the device so that the patient may be able to use the affected joint to a greater extent during the healing process. In this regard, the terms "proximal" and "distal" refer to locations of the bone and assembly relative to the insertion site of the assembly after it has been inserted into the bone. In other words, the proximal side of the fracture refers to a segment of bone closer to the site at which the intramedullary device assembly was inserted; the distal side of the fracture refers to a segment of bone farther from the insertion site, and so on. Thus, for ulnar applications at the olecranon, the terms proximal and distal will coincide with those terms as used to describe the human body. However, for ankle applications, for example, the terms will be reversed.

The compression member may be pre-adjusted such that the bone engagement member may be pushed against the proximal fragment as the intramedullary device is advanced into the medullary canal, as described below. In this way, at least partial compression at the fracture site may be provided without changing the position of the intramedullary device within the proximal fragment. Also in this way, the alignment of the bone segments may be provisionally held by the bone engagement member until more definitive fasteners are placed.

Referring to FIG. 1A, an intramedullary device assembly 10 according to one embodiment is shown in an expanded view. The assembly 10 includes an intramedullary device 12, a guide adapter 14, and a compression member 16 that may be attached end-to-end to treat a fracture, as described below. The intramedullary device 12 is configured (i.e., shaped and sized) to be inserted into the medullary canal of a bone and fastened to the bone on either side of the fracture. Thus, the particular configuration of the intramedullary device 12 may vary depending on the type and size of the bone to be treated. For example, an intramedullary device 12 to be used for fixing a fracture of an adult femur may have different dimensions and may be shaped differently than a device 12 to be used for fixing a fracture of a child's radius. Furthermore, the device 12 may be made of any absorbable or non-absorbable material that is compatible for use inside the human body, such as titanium, stainless steel, cobalt chrome, plastic, carbon fiber, or polymer.

In the embodiment shown in FIG. 1A, for example, the intramedullary device 12 is configured for use in an adult ulna via insertion through the olecranon. However, the intramedullary device 12 and assembly 10 may be used in various other locations in the human body, such as for repairing a fracture of the lateral malleolus (distal fibula) at the ankle. The intramedullary device 12 of FIG. 1A is tapered, with the proximal end (i.e., the end closest to the olecranon when installed) having a slightly larger diameter than the distal end (i.e., the end farthest from the olecranon when installed). Also, the intramedullary device may be tapered in the reversed manner or remain uniform in diameter throughout its length. Its axis may be straight, as shown in FIG. 1A, or curved. An ulna 18 and an olecranon 20 are illustrated in FIG. 2A, which shows an installed assembly 10 according to one embodiment. Referring again to FIG. 1A, the intramedullary device 12 may include a number of holes 22 configured to receive fasteners for fastening segments of bone to the intramedullary device 12. One or more of the holes 22 may be located towards the distal end of the intramedullary device 12, for example to fasten a bone segment that is on a distal side of the fracture to the intramedullary device 12, whereas one or more other holes 22 may be located towards the proximal end of the intramedullary device 12, for fastening another bone segment that is on a proximal side of the fracture, as discussed below. Furthermore, the holes 22 may be configured to receive various types of fasteners, such as pins, bolts, pegs, screws, and locking screws, among others. In some cases, the holes 22 may be internally threaded to receive corresponding externally threaded fasteners. As shown in FIG. 1B, the holes 22 may have a chamfered opening 23 on the side configured to receive a corresponding fastener which may aid insertion of the fastener by providing a larger opening to accept and guide the fastener.

Figure 3:
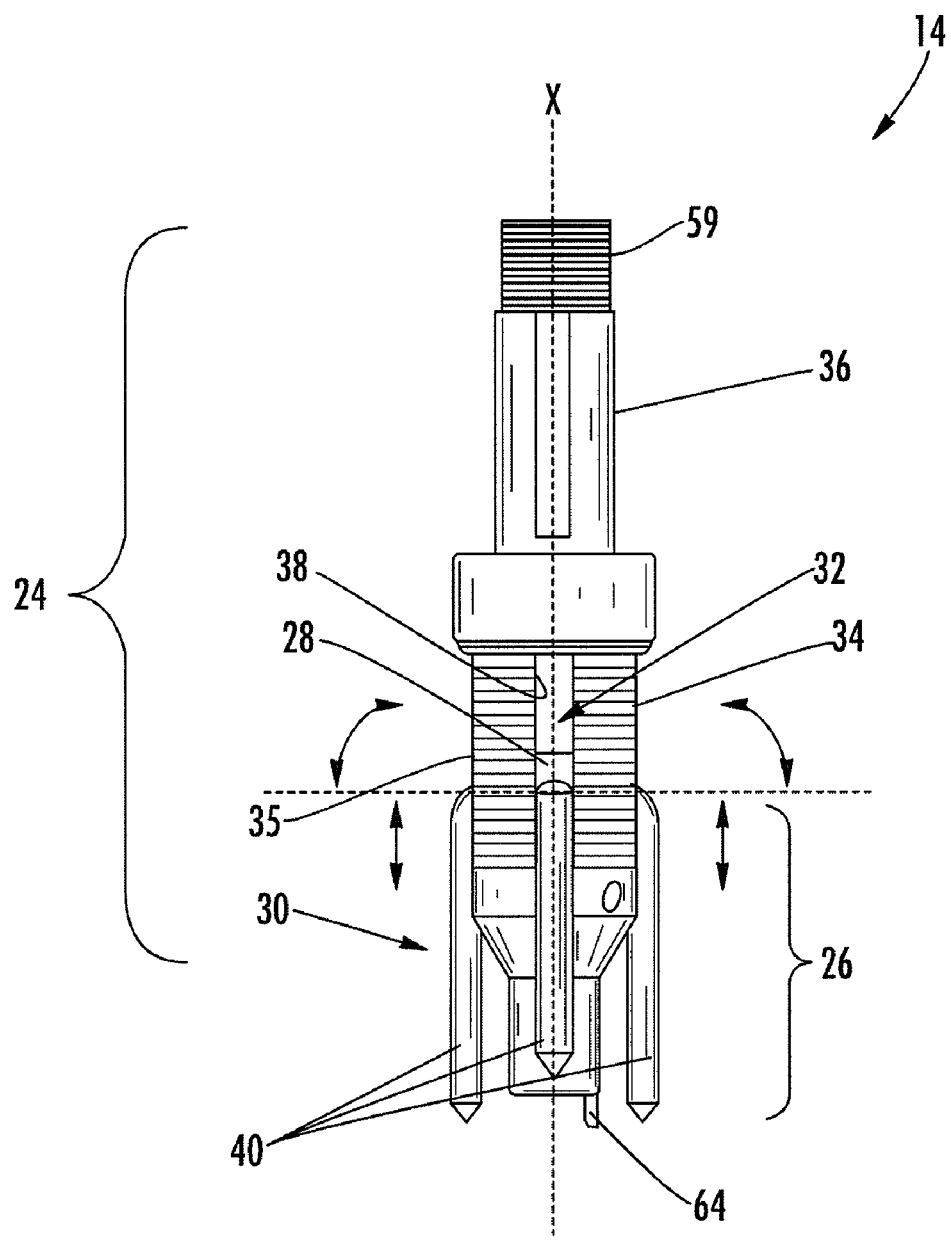
FIG. 3 is a side view of a guide adapter with pressing elements according to one embodiment.
Figure 6A:
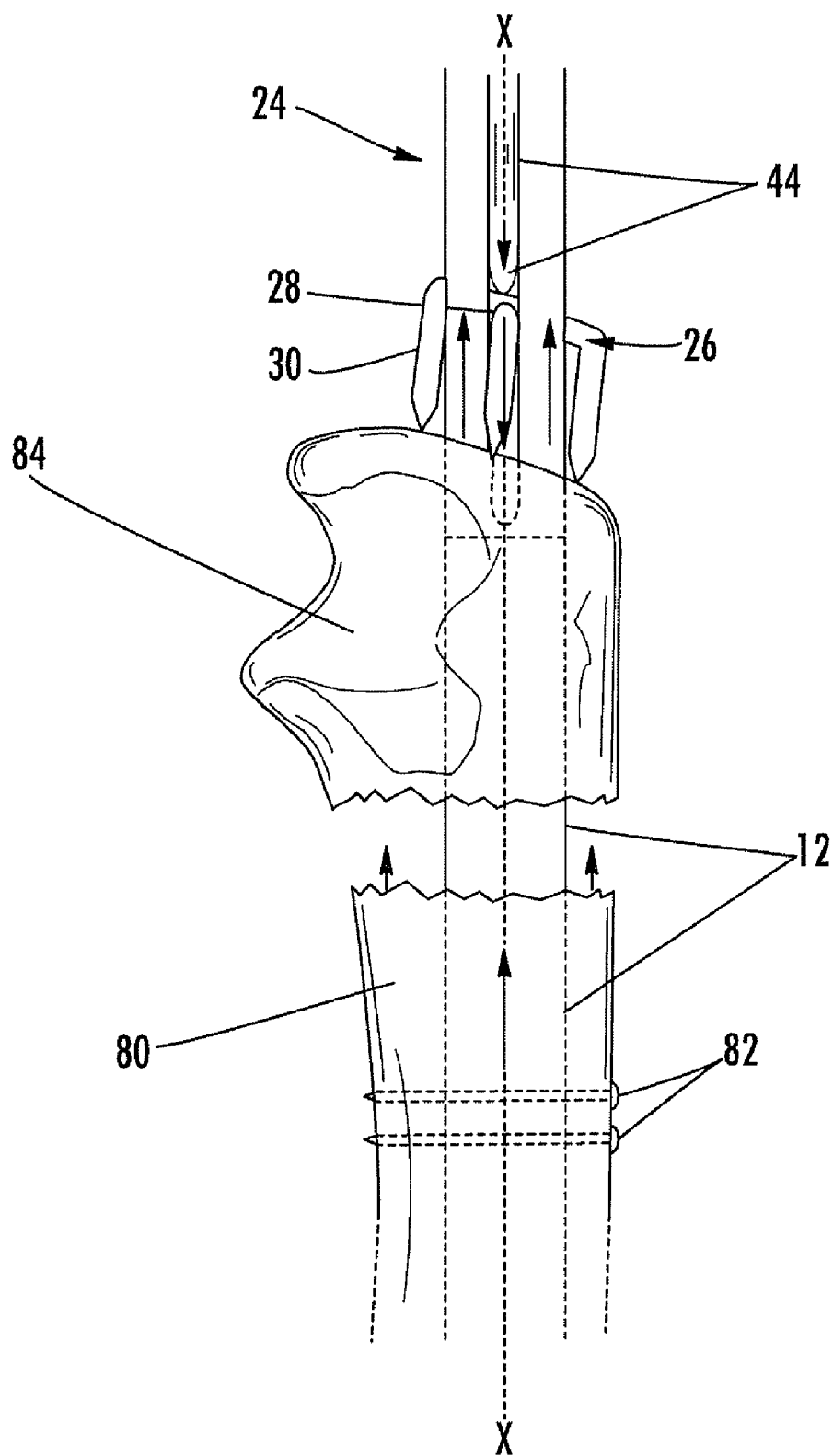
FIG. 6A is a partial side view of an installed intramedullary device assembly achieving compression according to one embodiment.

The guide adapter 14 of the assembly 10 includes a bone engagement member guide 24 and a bone engagement member 26, shown assembled according to one embodiment in FIG. 3. The bone engagement member guide 24 is configured to attach to an end of the intramedullary device 12, namely at the proximal end of the device 12, and to retain at least part of the bone engagement member 26 within the bone engagement member guide 24. For example, in the embodiment shown in FIG. 3, the bone engagement member 26 includes an internal part 28 that is configured to be movably retained within the bone engagement member guide 24 and an external part 30 that is configured to extend outside of the bone engagement member guide 24 and engage the end of the bone, as described below. In some cases, the guide adapter bone engagement member guide 24 defines an elongated void 32, such as within a cannulated portion of the bone engagement member guide, to allow the bone engagement member 26 to move along the bone engagement member guide 24. The bone engagement member 26 of the guide adapter 14 is configured to engage the end of the bone into which the intramedullary device 12 is inserted, as illustrated in FIGS. 2A and 6A. It is to be understood that the bone engagement member 26 may engage directly against the bone itself, soft tissue connected to the bone, or any other material found on the surface of the bone.

The bone engagement member includes at least two bone engagement points configured to engage the end of the bone. In FIG. 3, for example, the bone engagement points comprise the ends of the pressing elements 40, which are illustrated as three prongs, and which extend from the internal part 28 of the bone engagement member 26 towards the end of the bone. However, in other embodiments, the bone engagement points may be points on a continuous surface, such as two or more points on a single bone engaging element. For example, the bone engagement member 26 could comprise a flat ring or horseshoe-shaped pad depending from the internal part 28, and at least two separate geometrical points on this pad would be movable relative to each other in an axial direction when the bone engagement member tilts relative to the bone engagement member guide 24. In any case, at least one of the bone engagement points is permitted to move axially relative to at least one other bone engagement point such that it can more easily and securely engage the bone. As noted, the bone engagement member 26 may be tiltable with respect to an axis X of the bone engagement member guide 24, such that the bone engagement member 26 may tilt in any direction in order to engage a bone surface that may not be perpendicular to the X-axis, as indicated by the curved arrows in FIG. 3. An example of this is illustrated in FIG. 6A. In other embodiments, the bone engagement points may be defined on structures that are configured to bend, rotate and/or telescope (with or without tilting) in order to engage the end of the bone in a desirable orientation so that the compression forces applied may be more balanced.

Figure 2B:
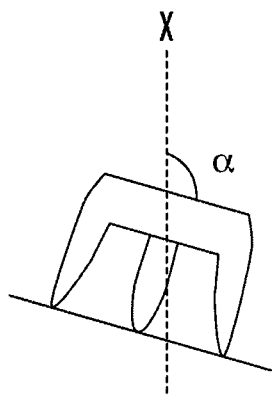
FIG. 2B shows engagement of a bone engagement member having pressing elements of equal length with a bone surface according to one embodiment.
Figure 2C:
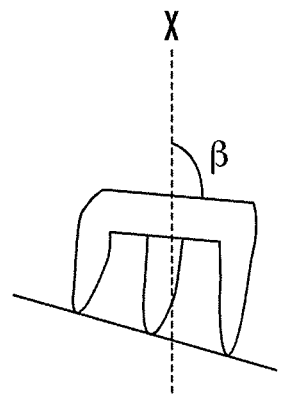
FIG. 2C shows engagement of a bone engagement member having pressing elements of unequal length with a bone surface according to another embodiment.
Figure 4:
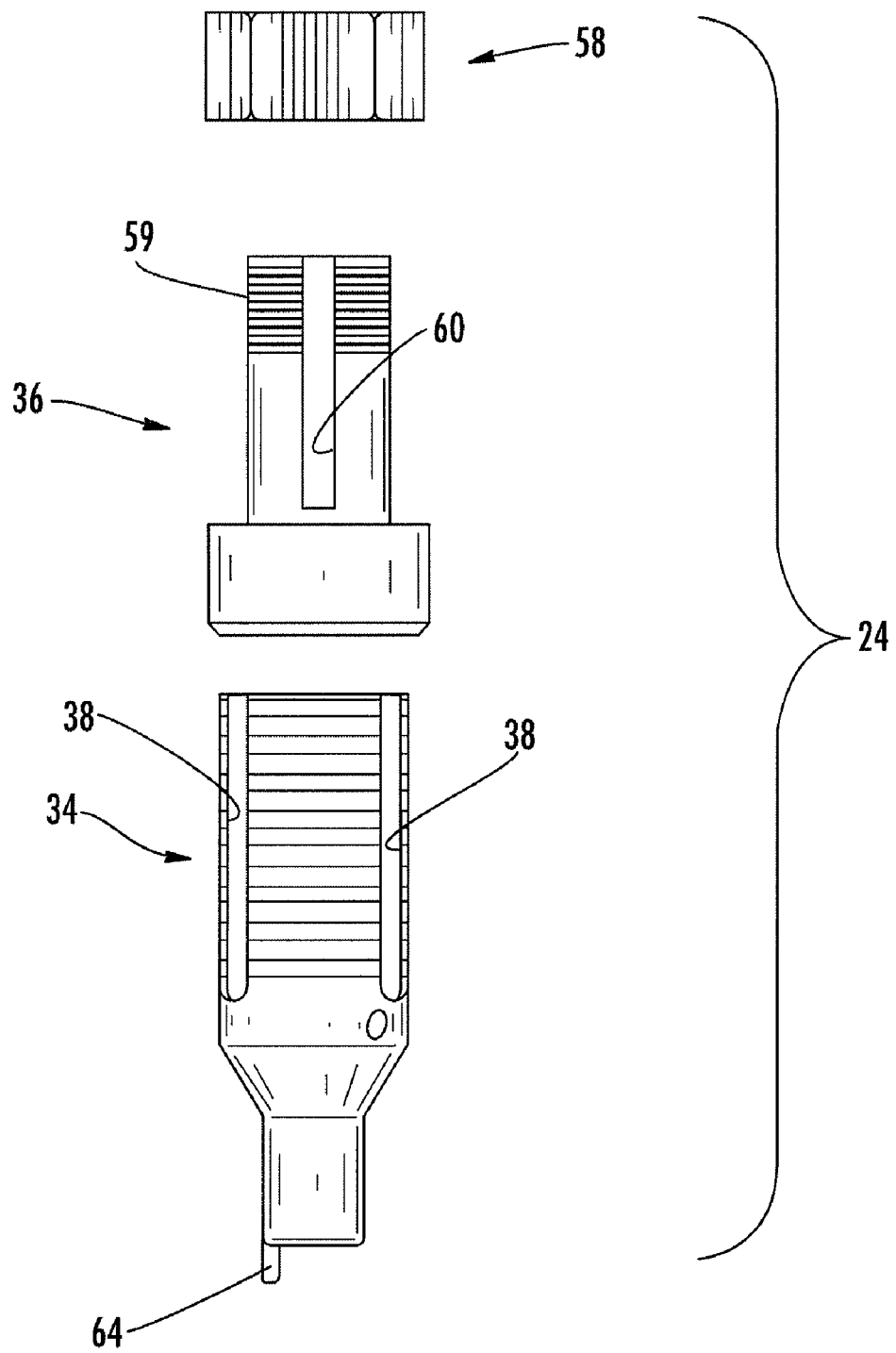
FIG. 4 is an expanded side view of a bone engagement member guide including multiple components according to one embodiment.

Referring to FIG. 4, the bone engagement member guide 24 may include more than one part that fit together or are otherwise connected to form the bone engagement member guide 24 around the bone engagement member (not shown). For example, the bone engagement member guide 24 may include a base portion 34 and an upper portion 36 that are welded together or otherwise fixedly attached after the bone engagement member 26 (shown in FIG. 3) or a portion thereof is placed within the base portion 34. In this regard, the base portion 34 may include one or more slots 38 through which the external part 30 of the bone engagement member 26 is configured to pass through. In the embodiment illustrated in FIG. 3, for example, three slots 38 (one visible) are defined in the base member 34, and the external part 30 of the bone engagement member 26 includes three pressing elements 40 that are configured to engage the end of the bone. Furthermore, at least one of these pressing elements 40 may be shorter than the other pressing elements in order to enhance the strength or stability of the engagement between the pressing elements and the end of the bone. In other words, differences in the length of the pressing elements may allow the pressing elements to conform to the angled surface of the bone while limiting the extent to which the bone engagement member must tilt to engage the bone. Thus, the angle of the internal part 28 of the bone engagement member 26 may remain closer to 90° with respect to the X-axis, providing for a more secure engagement with the bone. This is illustrated in FIGS. 2B and 2C, where the angle α (corresponding to pressing elements of equal length) is greater than the angle β (corresponding to pressing elements of unequal length). In other embodiments, the external part 30 may be configured differently.

The base portion 34 of the bone engagement member guide 24 may further include grooves 35 that provide a visual reference to a surgeon of how far the bone engagement member 26 has advanced towards the bone. For example, the grooves 35 may be equidistantly spaced at a certain interval, such as 1 mm apart. In this case, advancement of the bone engagement member 26 past 3 grooves would indicate that the bone engagement member 26 has advanced 3 mm.

Referring again to FIG. 1A, the compression member 16 of the assembly 10 is configured to attach to an end of the bone engagement member guide 24, opposite the end of the bone engagement member guide 24 that attaches to the intramedullary device 12. In some embodiments, the compression member 16 includes a pushing member 44, which may be integral to the compression member 16, as shown in FIG. 1A, or may be formed separately and subsequently attached to the compression member 16, for example via a welded or threaded connection. Regardless, the compression member 16 is movable along the bone engagement member guide 24 and is configured to move the bone engagement member 26 into engagement with the end of the bone (e.g., via the pushing member 44).

Figure 5A:
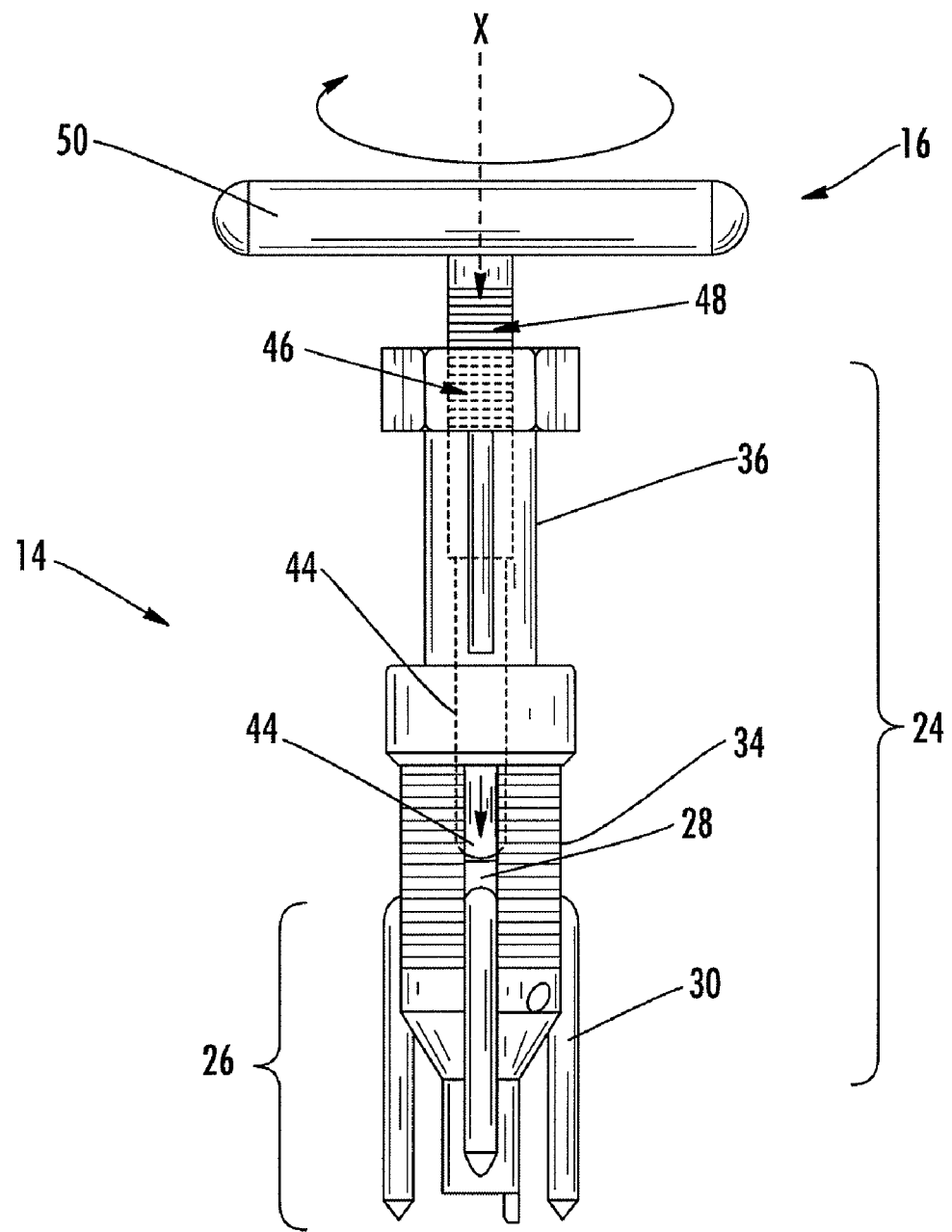
FIG. 5A is a side view of a guide adapter and compression member according to one embodiment.

For example, FIG. 5A shows a close-up view of the guide adapter 14 with the compression member 16 attached according to the embodiment illustrated in FIG. 1A. In this example, the upper portion 36 of the bone engagement member guide 24 may include an internally threaded region 46, and the compression member 16 may include a corresponding externally threaded region 48 that is configured to mate with the internal threads 46 of the bone engagement member guide 24. In this way, rotation of the compression member 16, such as by turning a handle 50 as indicated by the arrow, would serve to advance the compression member 16 and pushing member 44 farther into the bone engagement member guide 24, towards the bone engagement member 26. The handle 50 may have various configurations. For example, the handle 50 depicted in FIG. 1A has a "T" configuration, whereas the handle 50 depicted in FIG. 7A has a knob configuration. Optionally, the pushing member 44 may be pushed with or without a compressive member 16 manually or by electronic motor through the bone engagement member guide 24 toward the bone engagement member 26. There may be a locking mechanism between the compressive member 16 and/or pushing member 44 and the bone engagement member guide 24 to maintain the position of the compression member 16 against the bone engagement member 26.

Figure 5B:
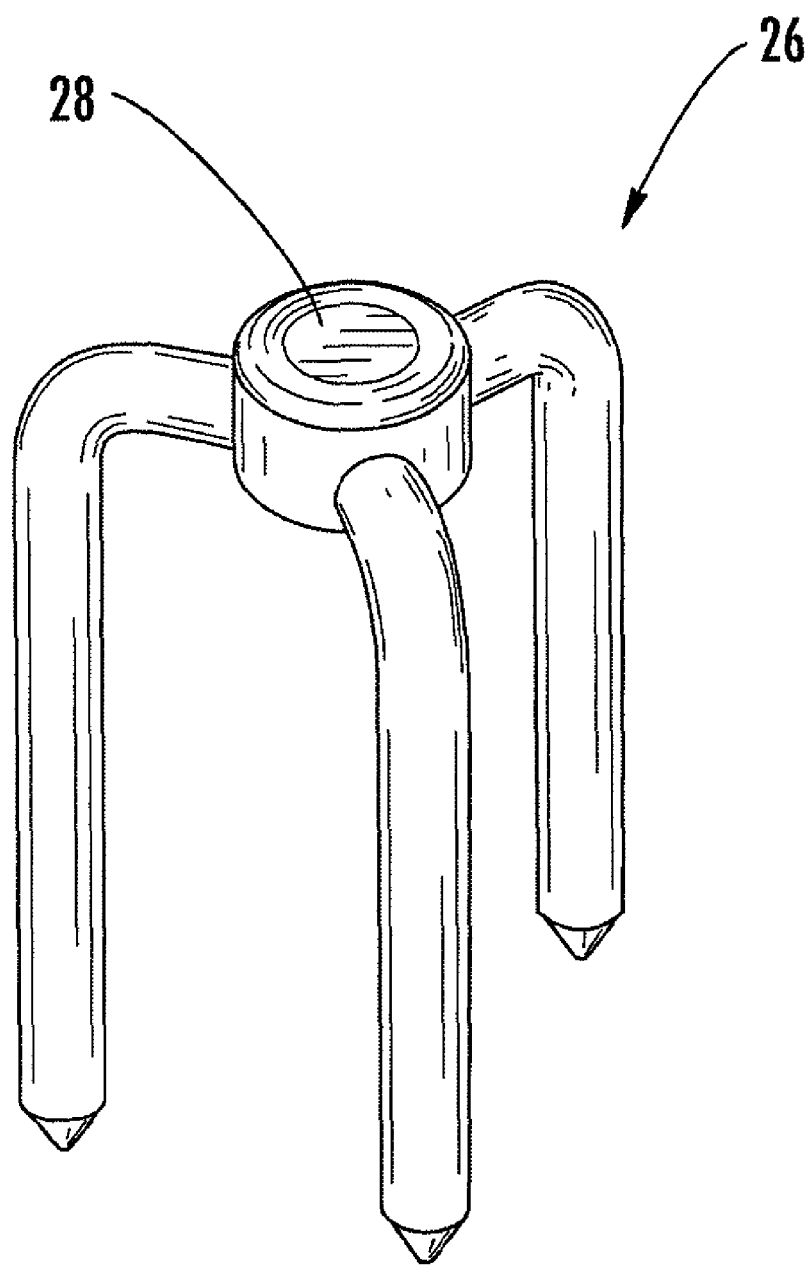
FIG. 5B is a perspective view of the bone engagement member according to the embodiment of FIG. 5A.

In an installed assembly 10 (shown in FIG. 6A), continued application of force by the pushing member 44 on the bone engagement member 26, for example, by continued rotation of the handle 50 after engagement of the bone engagement member 26 with the pushing member 44 and the bone, would serve to advance the bone engagement member 26 farther along the bone engagement member guide 24 in the direction of the intramedullary device 12. As a result, the intramedullary device 12, along with any attached bone segments, would be moved in the opposite direction (i.e., towards the compression member 16), thereby achieving compression as shown in FIG. 6A. In some embodiments, such as the one illustrated in FIG. 5A, the compression member 16 (e.g., via the pushing member 44) is configured to apply force to the internal part 28 of the bone engagement member 26. FIG. 5B shows the bone engagement member of FIG. 5A as it appears without the bone engagement member guide 24.

Figure 7C:
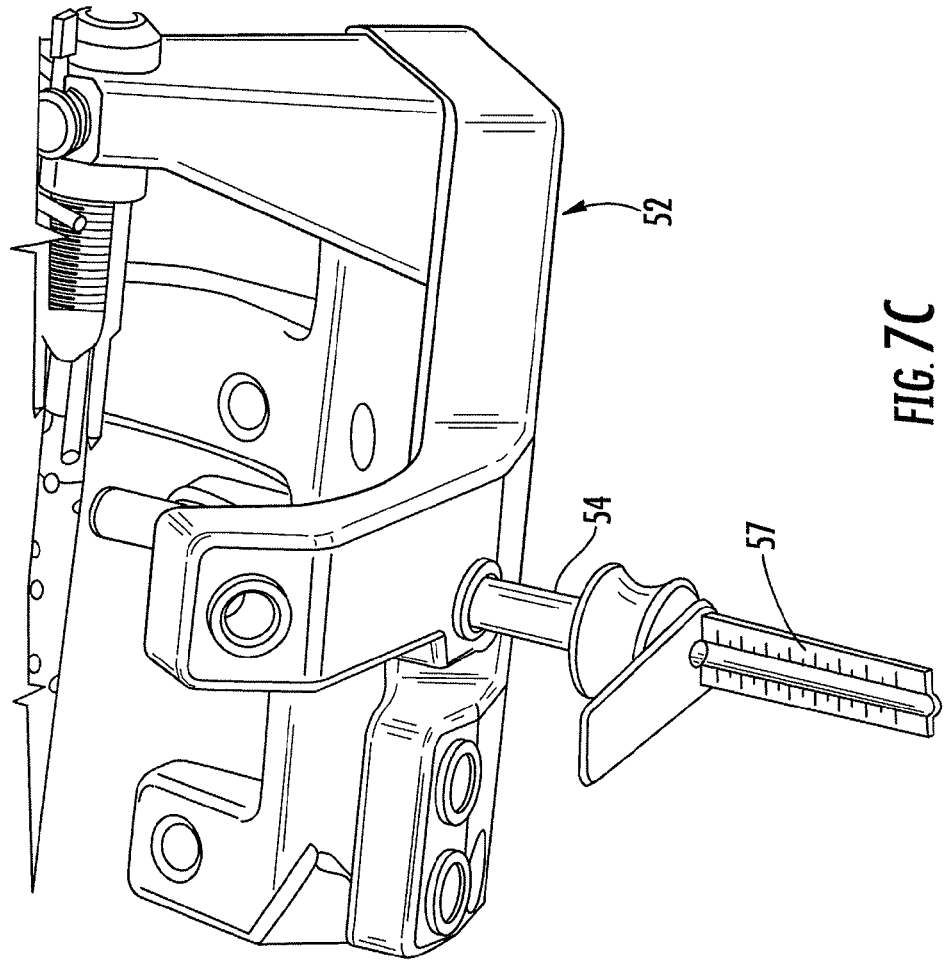
FIG. 7C is a perspective view of the drill guide with a cannula adapted to be used as a drill depth gauge.

The guide adapter 14 of the intramedullary device assembly 10 may be configured to attach to a drill guide 52, as illustrated in FIG. 7A. The drill guide 52 may be configured in various ways, depending on the configuration of the intramedullary device 12, the type of drill used (not shown), the doctor's preference, aesthetic appeal, durability and radiolucency of the materials, and other considerations. According to one embodiment, the drill guide 52 is formed of radiolucent plastic material. In general, the drill guide 52 may include cannulas 54 configured to guide the drill bit or other instruments used to secure fasteners to the bone in which the intramedullary device assembly 10 is installed. For example, in the treatment of a fractured ulna, the drill guide 52 may surround the patient's elbow and forearm once the assembly 10 is installed, and the drill bit may be inserted through a cannula 54 in order to maintain the angle at which the drill bit approaches the bone to facilitate proper drilling. Furthermore, the cannula 54 may act as a soft-tissue protector as it buries itself in the soft tissue (e.g., of the forearm) through minimally invasive puncture incisions and rests against the bone. This allows the drill bit to pass through and engage the bone without damaging the surrounding soft tissue structures. Each cannula 54 may be movable between guide holes 56 at various locations defined by the drill guide 52. In this regard, the guide holes 56 may be configured to be aligned with the holes 22 of the intramedullary device 12 (FIG. 1A), such that positioning the cannula 54 at a guide hole 56 facilitates the drilling of a hole through the bone that is aligned with a device hole 22, and a fastener may then be inserted to affix the drilled bone to the device 12. The drill guide cannulas 54 may further be configured to indicate the depth of the drill bit during the drilling operation by using depth indicating markings 57 on the cannula 54 as shown in FIG. 7C and possibly using a drill bit that is configured with depth markings that may be read at the entrance to the cannula 54.

The drill guide 52 may be attached to the guide adapter 14 in many ways. For example, referring to FIGS. 4, 7A, and 7B, the drill guide 52 may have a circular void in the connecting section 53 (shown in FIG. 7A) that is configured to slide over a corresponding part of the upper portion 36 of the bone engagement member guide 24 (shown in FIG. 4). A hex nut 58 or other type of end fastener may then be attached to the end of the upper portion 36, such as via external threads 59 on the upper portion 36 or via welding, to hold the drill guide 52 in place. Optionally, the drill guide 52 and the guide adaptor 14 may be fabricated from single piece of material so that the drill guide 52 and guide adaptor 14 are monolithic, rather than separately connected parts.

Figure 7B:
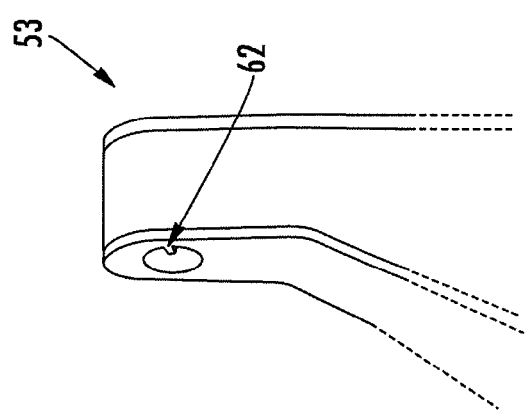
FIG. 7B is a close-up perspective view of a connecting section of the drill guide of FIG. 7A.
Figure 8:
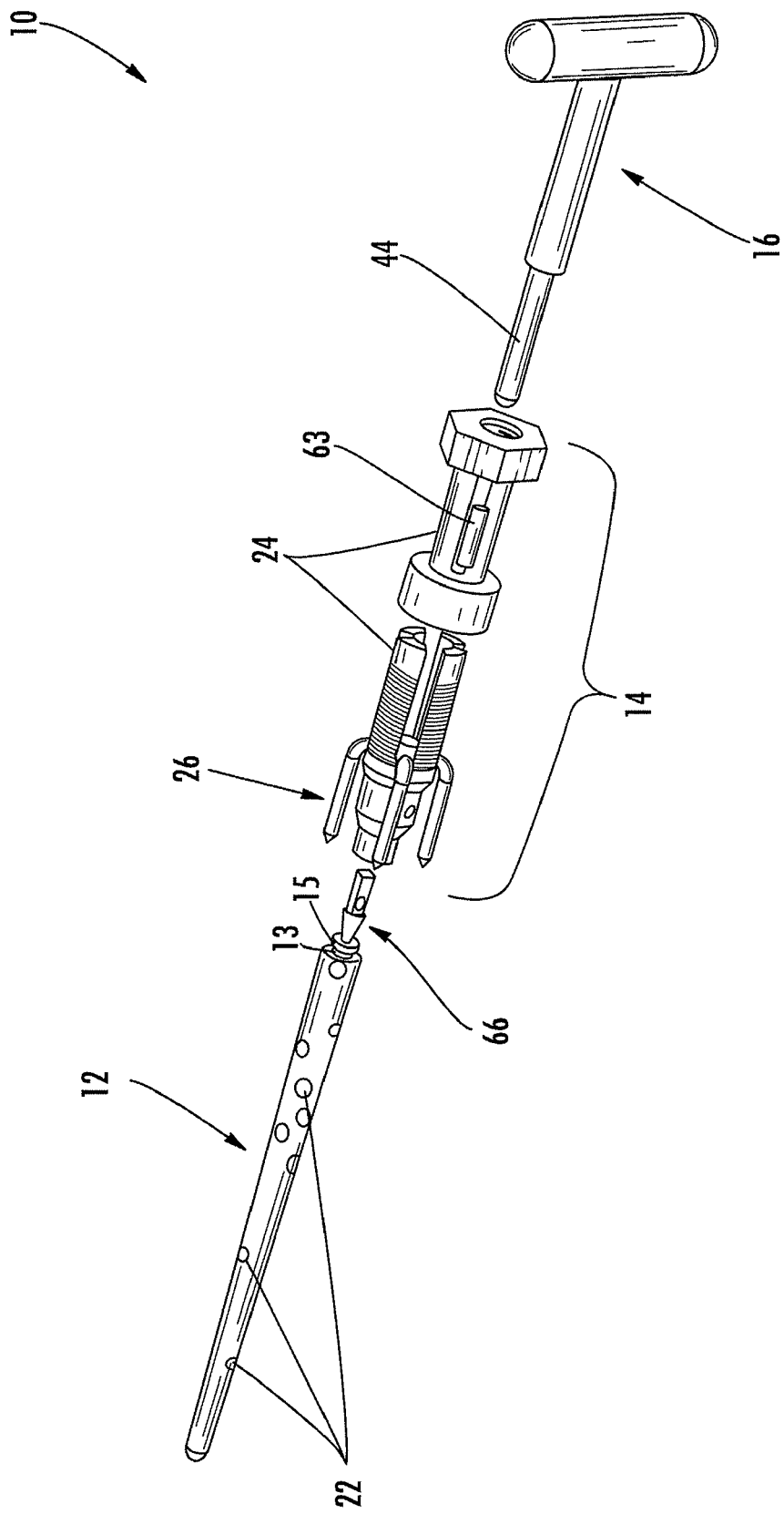
FIG. 8 is an expanded perspective view of an intramedullary device assembly including a breakaway stud according to one embodiment.

Furthermore, the bone engagement member guide 24 may define a keyway slot 60 (FIG. 4), for example in the upper portion 36, that is configured to permit alignment of the drill guide with respect to the bone engagement member guide 24 and the assembly 10 in general. In this case, the drill guide 52 would have a corresponding extension 62 formed in the void of the connecting section 53 (rather than a perfectly circular void for sliding onto the upper portion 36), as shown in FIG. 7B, that is configured to fit into the keyway slot 60 such that the drill guide 52 will only be received by the upper portion 36 in the proper orientation (i.e., with the extension 62 aligned to fit into the keyway slot 60). Alternatively, a separate adapter key 63 in the form of a rectangular bar, as shown in FIGS. 1A and 8, may be provided to prevent rotation of the guide adapter 14 relative to the drill guide 52. In this regard, a rectangular cross-section groove or slot that is aligned with the axis of the guide adapter 14 is milled in the outside surface of upper portion of the guide adapter 14. A corresponding slot is milled or broached into the drill guide 52 to be affixed to the guide adapter 14. The adapter key 63 may then be put into the slot of the guide adapter 14 such that is protrudes from the surface, as shown in the figures, and is able to engage the corresponding slot in the drill guide 52, thereby preventing rotation of the guide adapter 14 relative to the drill guide 52.

In some cases, such as in the embodiment of FIG. 7A, the drill guide 52 may include an external rotation guide 86 to provide a surgeon with a way to determine whether the intramedullary device 12 is being inserted into the medullary canal in the proper rotational orientation. If the device 12 is not at the proper rotation, some of the fasteners may be placed in suboptimal (or even deleterious) positions with respect to certain fracture types. The external rotation guide 86 may, for example, have an "X" configuration such that it may be used on different bones in the body. For instance, installing the intramedullary device 12 on a right elbow may require the surgeon to use one of the lines of the "X" for alignment, whereas installing the intramedullary device 12 on a left elbow may require the surgeon to use the other line. The cross-members of the "X" may be of square or rectangular cross section allowing an identifier such as "right" or "left" to be printed or etched onto each of the cross-members. Once the intramedullary device 12 is inserted into the canal, prior to drilling for screws, the proper rotation may be confirmed by lining up the plane of the external rotation guide 86 with the axis between the humeral epicondyles (in this example). The axis in this case should be approximately 10° from the horizontal relative to the joint line of the ulnohumeral joint. If the device 12 is rotated inappropriately, the respective line of the "X" will appear tilted away from the axis of the epicondyles, warning the surgeon that the position of the device 12 needs readjustment prior to drilling. The external rotation guide 86 may be removable (e.g., if the surgeon prefers other methods of confirming rotational alignment), and the position of the external rotation guide 86 may be adjustable such that it may be raised or lowered to correspond to the humeral epicondylar axis of the particular patient.

Figure 10A:
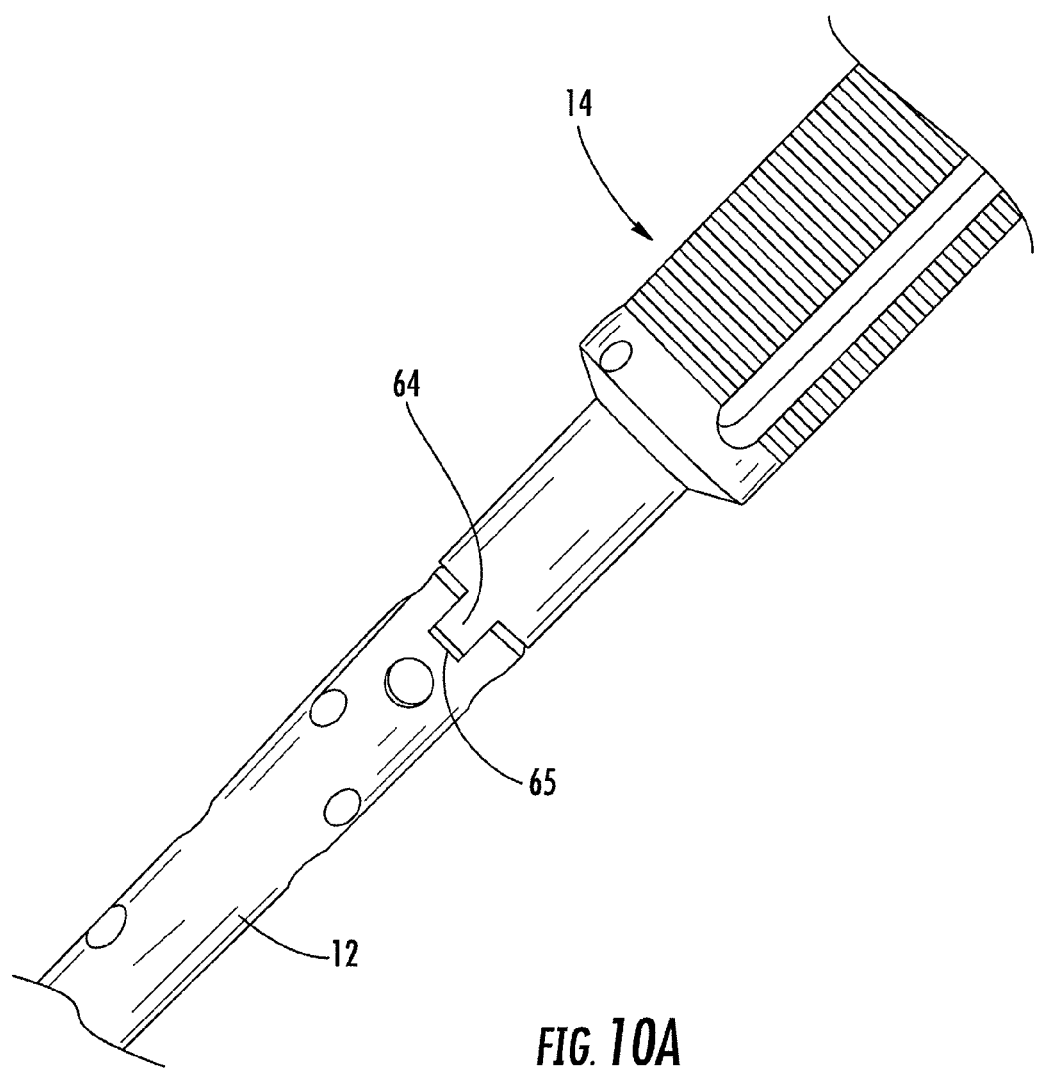
FIG. 10A is a perspective view of the intramedullary device and guide adapter showing the tab of the guide adapter according to one embodiment.

Referring to FIGS. 3, 4, and 10A, the guide adapter 14 may also include a tab 64 or other protrusion configured to engage the intramedullary device 12 to limit rotation of the guide adapter 14 with respect to the intramedullary device 12. In this regard, the tab 64 may be configured to fit in a corresponding notch 65 in the attachment end of the intramedullary device 12 such that the guide adapter 14 and the intramedullary device 12 may only be attached when the tab 64 is aligned with the corresponding notch 65, and, once attached, torsion and bending forces across the junction may be controlled. Optionally, the intramedullary device 12 may include a tab or other protrusion configured to engage a corresponding notch in the guide adapter 14 to limit rotation of the guide adapter 14 with respect to the intramedullary device 12 and to control torsion and bending forces across the junction.

In some embodiments, such as the one illustrated in FIG. 8, the intramedullary device assembly 10 includes a breakaway stud 66 connecting the intramedullary device 12 and the guide adapter 14. The breakaway stud 66 is configured to break away from the intramedullary device when a predetermined amount of force is applied to the breakaway stud 66. Referring to FIGS. 9A and 9B, for example, the breakaway stud 66 may include a proximal portion 68 and a distal portion 70. The proximal portion 68 is configured to engage the bone engagement member guide such that the bone engagement member guide is rotationally fixed with respect to the breakaway stud 66. For example, the proximal portion 68 may have a slab-like or domino shape, as seen in FIG. 9A, that is configured to fit into a corresponding recess in the guide adapter 14 such that rotation between the guide adapter 14 and the breakaway stud 66 is controlled. The proximal portion 68 in some cases defines a ridge that fits into a slot formed in the recess of the guide adapter 14 or is otherwise configured such that the breakaway stud 66 can only be received in the recess in a certain orientation.

The distal portion 70 is configured to engage the intramedullary device and includes a region of concentrated stress 72 that allows the force applied to the breakaway stud 66 to be focused in the region of concentrated stress 72 and causes the breakaway stud 66 to break at or near the region of concentrated stress 72. The distal portion 70 may be configured in various ways. For example, as shown in FIG. 9B, the distal portion 70 may be conically-shaped and may be tapered. Thus, in the embodiment of FIG. 9B, the region of concentrated stress 72 may be the region where the cross-sectional area of the tapered portion 70 is smallest. Alternatively, the region of concentrated stress 72 may include a "shark-bite" or other type of reduction in cross-section. In this way, once the assembly 10 has been installed in the medullary canal of the fractured bone, compression of the fracture has been achieved, and the bone segments of the fracture have been fastened to the intramedullary device such that the fracture can heal, the guide adapter 14 and compression member 16 may be detached from the rest of the assembly. The breakaway stud 66 may then be removed by applying a predetermined force to the breakaway stud 66 leaving the intramedullary device 12 installed in the bone to facilitate healing and at the same time allowing the patient to use the affected joint and bone to the extent possible. In some embodiments, the breakaway stud 66 may be broken away before the guide adapter 14 is removed from the assembly.

In some cases, the region of concentrated stress 72 may include an undercut in the distal portion 70 where the breakaway stud 66 attaches to the intramedullary device 12 such that upon detachment (i.e., breaking of the breakaway stud 66), any residual portion of the stud 66 that remains attached to the intramedullary device 12 is recessed into the device 12. In this way, the residual stud is less palpable to the patient and the potential for soft tissue irritation is reduced.

The intramedullary assembly 10 need not, however, include a breakaway stud 66 to allow detachment of the guide adapter 14 and the compression member 16 from the intramedullary device 12. The guide adapter 14 and the compression member 16 may detach in other ways, such as via a screw connection that is unscrewed once the installation is complete.

Figure 9C:
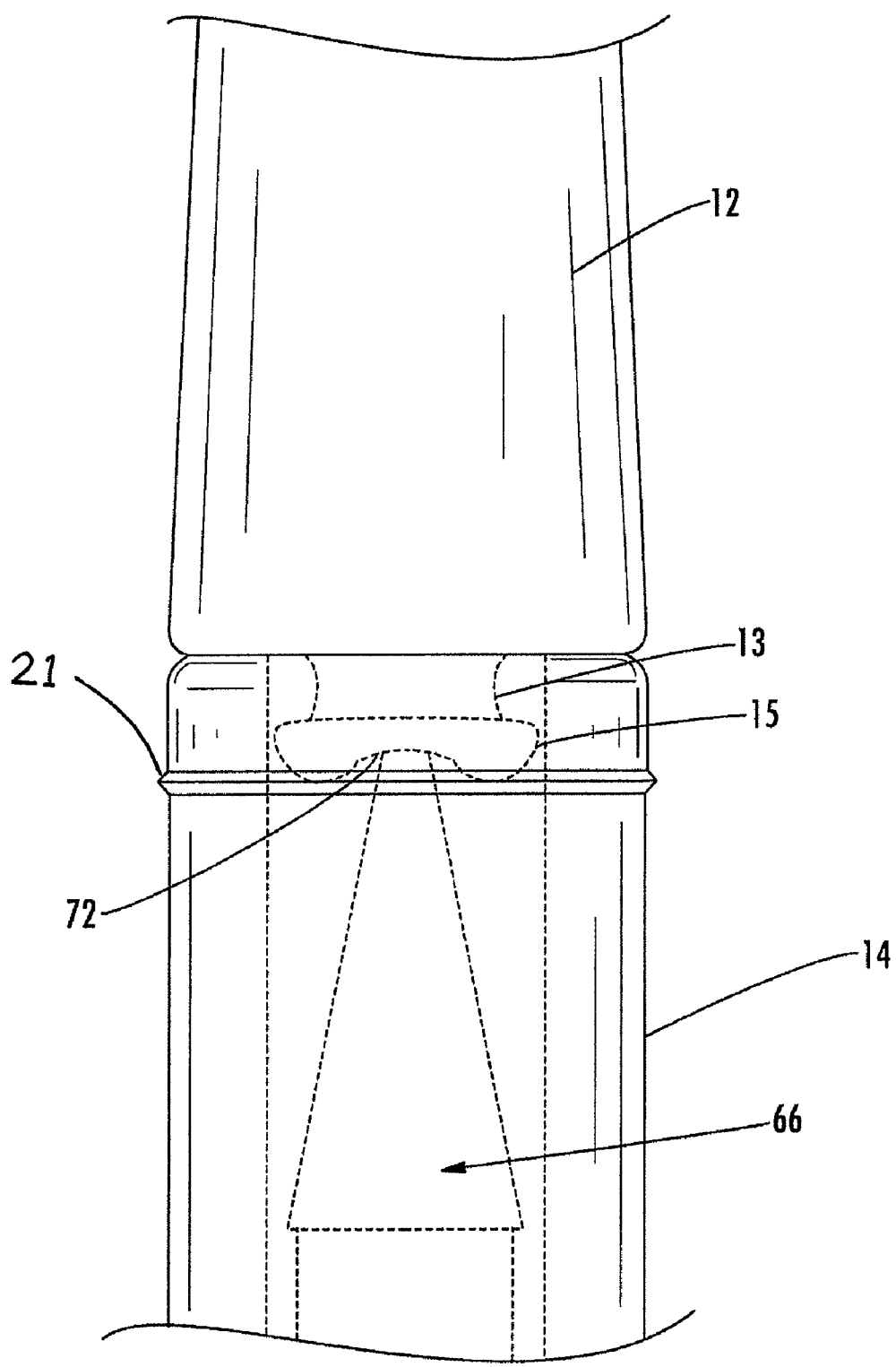
FIG. 9C is a side plan view of the breakaway stud and nub within the guide adapter.

In some embodiments, the proximal end of the intramedullary device 12 may define a short stump or nub 13 for attaching the breakaway stud 66, as shown in FIGS. 8 and 9B. The nub 13 may have a circumferential lip 15 that fits partially into the bone engagement member guide of the guide adapter 14 so as to offset some of the bending forces that the intramedullary device 12 may experience during installation in the bone. Furthermore, the lip 15 may allow for the intramedullary device 12 to be manipulated after installation, for example to facilitate removal of the intramedullary device 12 from the bone if removal becomes necessary or desirable. In this case, in order to break the breakaway stud 66 to detach the intramedullary device 12 from the rest of the assembly, the guide adapter 14 must be disengaged from the lip 15 before force can be applied to the region of concentrated stress 72. The guide adapter 14 may include a ridge 21 around the circumference, or a similar indicator, to indicate the location of the end of the nub 13 within the guide adapter 14 as shown in FIG. 9C. This ridge or marking would serve to indicate the depth to which the intramedullary device 12 must be inserted to prevent the nub 13 from protruding from the end of the bone.

Figure 10B:
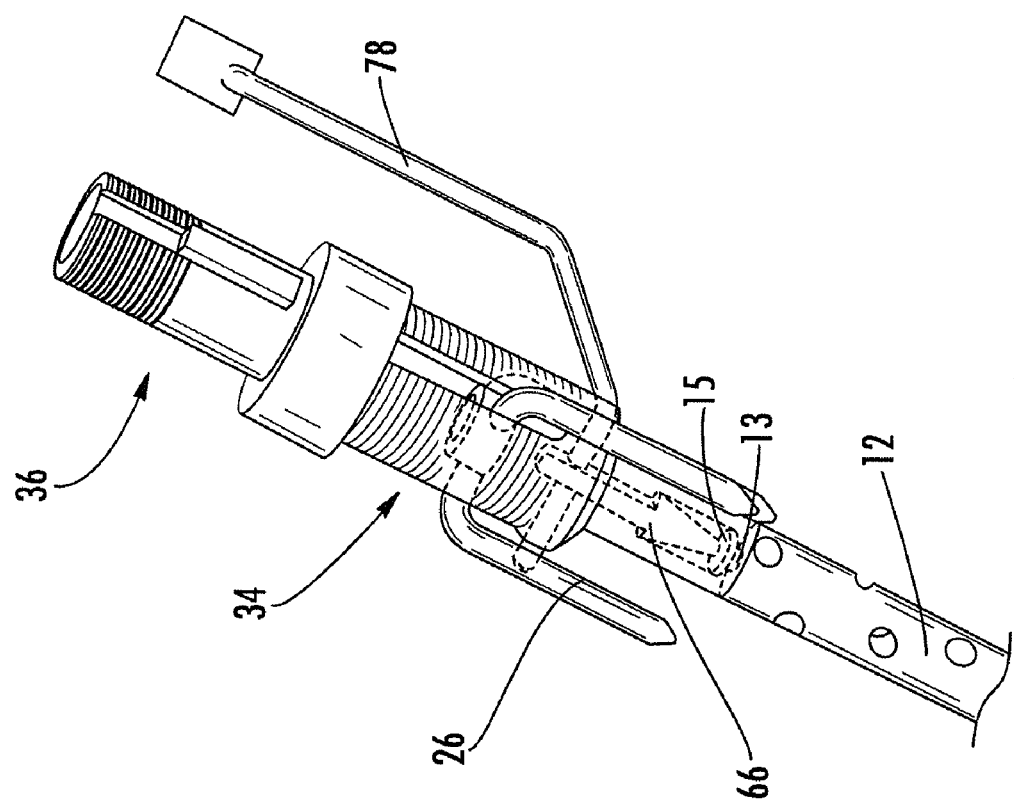
FIG. 10B is a perspective view showing the intramedullary device, breakaway stud, and guide adapter of FIG. 10A in an assembled configuration.

The bone engagement member guide 24 of the guide adapter 14 may define a transverse locking hole 74, and the breakaway stud 66 may define a corresponding transverse locking hole 76, as shown in FIG. 9A. When the guide adapter 14 and the breakaway stud 66 are assembled, the respective transverse locking holes 74, 76 may be aligned and thus configured to receive a locking mechanism 78, such as the pin illustrated, that serves to lock the guide adapter 14 and the breakaway stud 66 to each other when the locking mechanism 78 is in place. Referring to FIG. 10B, installation of the locking mechanism 78 functions to hold the intramedullary device 12 against the guide adapter 14 and to maintain rotational stability at the junction during installation of the assembly in the bone. A catch 79 may be provided on the connecting section 53 of the drill guide 52 to hold the mechanism 78 in place during manipulation of the assembly 10, as illustrated in FIG. 7A. Upon detaching the intramedullary device 12 from the guide adapter 14, the locking mechanism 78 may be removed so as to allow the intramedullary device to disengage from the guide adapter (i.e., to allow the lip 15 of the nub 13 to disengage from the bone engagement member guide), as previously discussed. At this point, bending forces, either along the axis or laterally thereto, and/or axial loads may be applied to the assembly to break the breakaway stud 66 at the region of concentrated stress 72 (FIG. 9B) and detach the intramedullary device 12 from the rest of the assembly.

In other embodiments, a method for assembling an intramedullary device assembly for repairing a defect (or defects) of a bone is provided. Referring to FIG. 1A, initially, an intramedullary device 12 configured to be inserted into a medullary canal of a bone is provided. As previously described, the intramedullary device 12 may have various configurations, depending on the location and type of bone as well as other considerations. The medullary canal of the bone may, in some cases, be prepared beforehand for receiving the intramedullary device 12 using tools and methods known by those skilled in the art, such as by drilling out the medullary canal so that the dimensions of the medullary canal correspond to the dimensions of the intramedullary device 12. The intramedullary device 12 may then be inserted into the prepared medullary canal of the bone. For example, referring to FIG. 2A, the intramedullary device 12 may be inserted into the medullary canal of a fractured ulna 18 through the metaphyseal end of ulna, or the olecranon 20. As another example, the intramedullary device 12 may be inserted into the medullary canal of a fractured fibula through the metaphyseal end of the fibula, or the lateral malleolus. The intramedullary device may also be configured so that it cuts its own path into the bone with or without the assistance of accessory tools.

Referring again to FIG. 1A, the guide adapter 14 is attached to a proximal end of the intramedullary device 12, either before or after insertion of the intramedullary device 12 into the medullary canal. As previously described, the guide adapter 14 includes a bone engagement member guide 24 having a first end configured to attach to the proximal end of the intramedullary device 12 and a bone engagement member 26 that is movable along the bone engagement member guide 24 and includes at least two bone engagement points. At least one bone engagement point is movable along an axis of the bone engagement member guide 24 relative to at least one other bone engagement point and is configured to engage an end of the bone. For example, the bone engagement member guide 24 may be tiltable with respect to an axis X of the bone engagement member guide 24, as shown in FIGS. 2A, 2B, and 2C, or one or more of the bone engagement points may be defined on a structure, such as a discrete pressing element, that can bend, rotate, or telescope to engage the bone.

As described above, the bone engagement member guide 24 may be made up of one or more components. The bone engagement member 26 of the guide adapter 14 is configured to engage the end of a bone. For example, in FIG. 3, the bone engagement member 26 includes multiple pressing elements 40 configured to engage the surface of the end of the bone (as illustrated in FIGS. 2A and 6A). Turning again to FIG. 1A, a compression member 16, which is movable along the bone engagement member guide 24, is attached to the second end of the bone engagement member guide 24 (for example, as shown in FIG. 5A).

A drill guide 52, shown in FIG. 7A, may also be attached to the guide adapter 14, for example, as previously described with reference to FIGS. 4 and 7A. The drill guide 52 may be configured to allow the drilling of holes through the bone (i.e., through the patient's soft tissues and into the bone) such that the drilled holes are in alignment with corresponding holes defined by the intramedullary device 12. In this way, fasteners such as screws, pegs, bolts, pins or other fasteners may be inserted through the holes in the bone and received by the corresponding holes in the intramedullary device to hold the bone to the intramedullary device in those locations.

In some embodiments, such as the embodiment of FIGS. 8 and 9A, a breakaway stud 66 may be used to attach the guide adapter 14 to the proximal end of the intramedullary device 12. In this regard, one end of the breakaway stud 66 may be attached to the proximal end of the intramedullary device 12, and the other end of the breakaway stud 66 may be attached to the first end of the bone engagement member guide 24. As mentioned above, a locking mechanism 78 may be used to hold the breakaway stud 66 and the guide adapter 14 together via transverse locking holes 74, 76, and a lip 15 of the intramedullary device 12 may engage the guide adapter 14 for additional support, as shown in FIG. 10B.

Once the intramedullary device assembly 10 is assembled and installed in the medullary canal of the affected bone, regardless of the order of the steps, compression may be applied to bring the bone segments on either side of the fracture together, thereby promoting the healing of the bone. According to one embodiment of a method of applying compression, the intramedullary device is inserted into a medullary canal of the bone, for example, as previously described. Referring to FIG. 6A, the intramedullary device 12 is fastened to a distal segment 80 of the bone (a segment located on the distal side of the bone defect relative to the intramedullary device assembly). For example, one or more locking screws 82 may be inserted through intramedullary device holes 22 (shown in FIGS. 1A and 8) to hold the distal segment 80 to the intramedullary device 12.

Compression may then be applied by advancing the compression member 16 towards the intramedullary device and bone (illustrated in FIG. 5A and indicated by the downward arrow) and into engagement with the bone engagement member 26. For example, in FIG. 5A, the handle 50 of the compression member 16 may be rotated to advance the pushing member 44 into engagement with the bone engagement member 26. As a result, the bone engagement member 26 advances towards the bone, engages the end of the bone, and continues to advance along the bone engagement member guide towards the intramedullary device 12, as illustrated in FIG. 6A, such that the distal segment 80 is moved towards the proximal segment 84 of the bone (i.e., the segment of bone located on the proximal side of the fracture relative to the intramedullary device assembly). The relative movement of the compression member 16, the bone engagement member 26, the bone engagement member guide 24, the intramedullary device 12, and the distal segment 80 are shown in FIG. 6A with arrows on the respective elements.

Figure 6B:
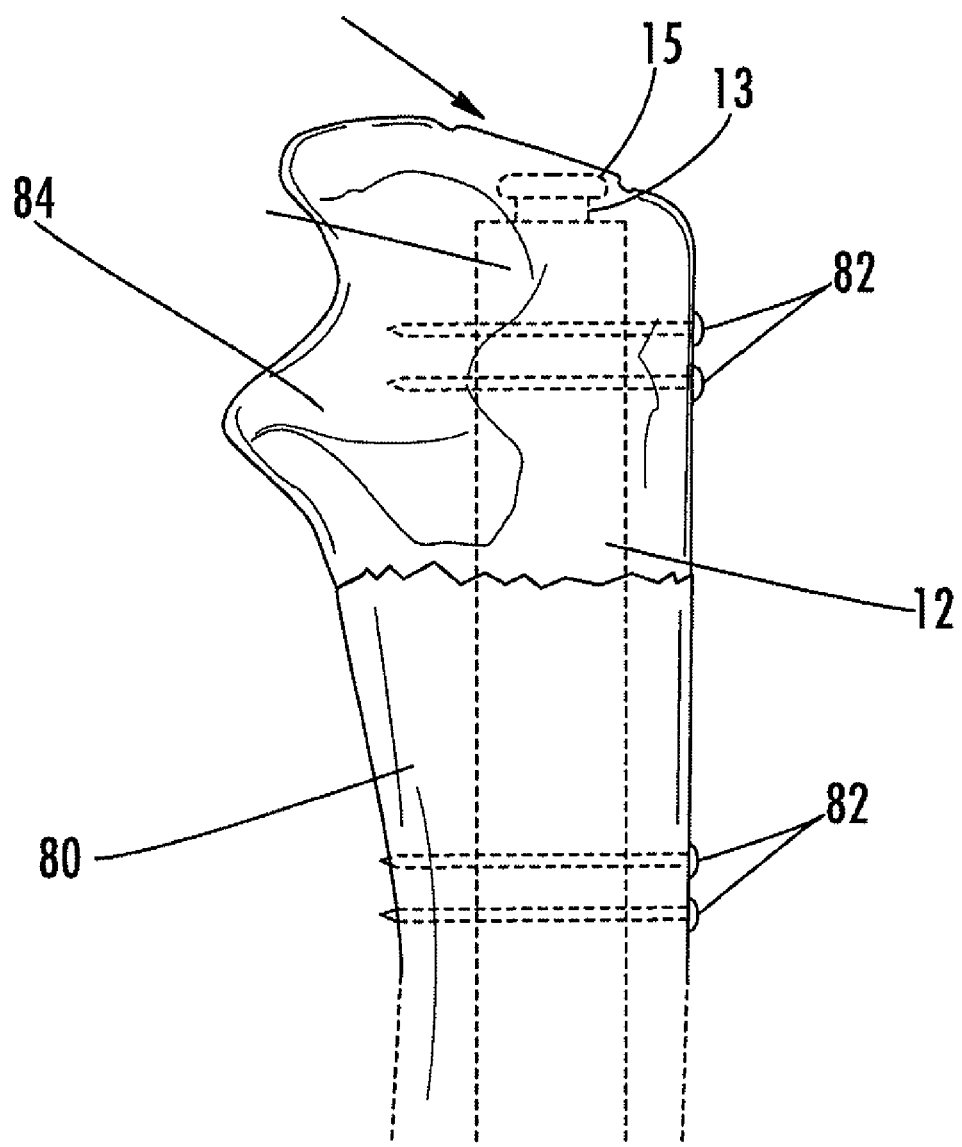
FIG. 6B is a partial side view of an installed intramedullary device of FIG. 6A after desired compression has been achieved and the guide adapter and compression member have been detached.

Referring to FIG. 6B, after the desired amount of compression has been achieved, the intramedullary device 12 may be fastened to the proximal segment 84 to maintain compression of the distal and proximal segments 80, 84. For example, screws, pegs, bolts, pins or other fasteners 82 may be inserted into holes in the intramedullary device 12, bicortically and/or unicortically, to fasten the proximal segment 84 to the intramedullary device 12. In some embodiments, the holes in the distal and/or proximal portions of the intramedullary device 12 may have internal threads (or another type of capturing mechanism) that are configured to engage external threads (or a corresponding capturing mechanism) of the fasteners. Although FIGS. 6A and 6B show the screws 82 in this example placed transversely to the device 12 and parallel to the other screws 82, the screws 82 or other fasteners may have various orientations according to the configuration of the receiving holes in the intramedullary device 12 and other considerations to allow for proper fastening between the bone and the intramedullary device 12.

In other embodiments, the proximal segment 84 may be provisionally fixed at intramedullary assembly before compression is applied at the fracture such that compression at the fracture site may be provided without changing the position of the intramedullary device within the proximal segment. In this regard, the compression member may be pre-adjusted such that the bone engagement member is set at a pre-determined point along the guide adapter. Thus, as the intramedullary device is advanced into the medullary canal of the proximal bone segment 84, the bone engagement member is pushed against the end of the bone and the intramedullary device is placed in the correct position in the proximal segment (i.e., the proximal end of the device is aligned flush with the cortex). The entire intramedullary guide assembly may then be pushed toward the distal segment 80, while providing the ability for the surgeon to manually control and adjust the path of advancement of the proximal bone segment 84 towards the distal bone segment 80 by slight rotational or lateral movements of the intramedullary guide assembly until a desired level of initial compression is achieved at the fracture site. The position of the intramedullary device may be adjusted if necessary via the compression member. By pushing the two bone fragments together in this way, the intramedullary device assembly provisionally holds the fracture reduced until the distal screws are in place. If more compression is required, the compression member may be advanced farther along the bone engagement member guide (towards the bone). Once the appropriate amount of compression is achieved, the proximal screws may be put in place.

In any case, the guide adapter, compression member, and other attached accessories (such as the drill guide) may not be needed once the desired amount of compression has been achieved and the intramedullary device 12 has been fastened to the distal and proximal segments 80, 84 of the bone. As a result, the first end of the bone engagement member guide may be detached from the intramedullary device 12, for example by unthreading the bone engagement member guide from the intramedullary device 12. In this way, the intramedullary device 12 may remain in the medullary canal of the bone, with the bone segments 80, 84 attached to facilitate stabilization of the defect and proper healing, and, at the same time, extraneous components of the assembly may be removed to provide a relatively unobstructed surface of the bone and allow the patient to use the affected part to the extent possible with greater comfort.

In embodiments that include a breakaway stud (FIGS. 8, 9A, and 9B), the guide adapter 14 and the compression member 16 may be detached from the inserted and fastened intramedullary device 12 by removing a locking mechanism before applying force to break the breakaway stud 66 (for example, at the region of concentrated stress 72). For example, referring to FIGS. 9A, 9B, and 10B, the locking mechanism 78 may need to be removed from the holes 74, 76 so that the intramedullary device 12 may be disengaged from the guide adapter 14 (i.e., by disengaging the lip 15). Once disengaged, force may be applied to the assembly to break the breakaway stud 66 and separate the intramedullary device 12 from the rest of the assembly. Furthermore, if removal of the intramedullary device 12 from the bone is required at some later time, the lip 15 may be used to withdraw the intramedullary device 12 from the medullary canal, as previously discussed.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An intramedullary device assembly for repairing a defect of a bone, the assembly comprising:
    an intramedullary device configured to be inserted into a medullary canal of the bone and secured to the bone on either side of the defect;
    a bone engagement member guide removably attached to an end of the intramedullary device;
    a compression member that is movable along the bone engagement member guide; and
    a bone engagement member that is movable along the bone engagement member guide by the compression member, wherein at least a portion of the bone engagement member is disposed within the bone engagement member guide, wherein the bone engagement member defines at least two bone engagement points and wherein at least one bone engagement point is movable relative to at least one other bone engagement point in the direction of the bone;
    wherein the compression member forces the bone engagement member in the direction of the bone along the bone engagement member guide and the at least one bone engagement point is permitted to move relative to the other at least one bone engagement point so that both bone engagement points can engage an end of the bone as compression is applied to the bone.

2. The intramedullary device assembly of claim 1, wherein the bone engagement member further comprises at least two pressing elements, and wherein at least two of the pressing elements are rigidly connected together and define the bone engagement points, and wherein the relative motion between the bone engagement points is caused by rotation of the bone engagement member relative to the bone engagement member guide.

3. The intramedullary device assembly of claim 1, wherein the bone engagement member further comprises at least two pressing elements, and wherein at least two of the pressing elements are rigidly connected together and define the bone engagement points, and further wherein at least one of the pressing elements is extensible so that the relative motion between the bone engagement points is caused by extension of the at least one pressing element.

4. The intramedullary device assembly of claim 1, wherein the bone engagement member guide defines an elongated void, and wherein the bone engagement member includes an internal part configured to be movably retained within the elongated void of the bone engagement member guide and an external part configured to extend outside of the elongated void of the bone engagement member guide and engage the end of the bone via the at least two bone engagement points.

5. The intramedullary device assembly of claim 4, wherein the compression member is configured to apply force to the internal part of the bone engagement member.

6. The intramedullary device assembly of claim 4, wherein the external part of the bone engagement member comprises at least one pressing element configured to engage the end of the bone and a bone engagement point is defined at the end of the at least one pressing element.

7. The intramedullary device assembly of claim 6, wherein the external part of the bone engagement member comprises at least two pressing elements each defining a bone engagement point, and at least one of the pressing elements is shorter than at least one other pressing element.

8. The intramedullary device assembly of claim 1, wherein the bone engagement member guide is configured to attach to a drill guide.

9. The intramedullary device assembly of claim 8, wherein the drill guide is configured to receive a cannula.

10. The intramedullary device assembly of claim 9, wherein the cannula is configured to serve as a depth gauge.

11. The intramedullary device assembly of claim 8, wherein the bone engagement member guide defines a keyway slot configured to permit alignment of the drill guide with respect to the intramedullary device assembly.

12. The intramedullary device assembly of claim 11, wherein an external rotation guide is attached to the drill guide.

13. The intramedullary device assembly of claim 1 further comprising a breakaway stud connecting the intramedullary device and the bone engagement member guide, wherein the breakaway stud is configured to break when a predetermined amount of force is applied to the intramedullary device assembly such that the breakaway stud can be removed from the intramedullary device.

14. The intramedullary device assembly of claim 13, wherein the breakaway stud is configured to fit in a corresponding recess in the bone engagement member guide such that rotation of the bone engagement member guide with respect to the intramedullary device is prevented.

15. The intramedullary device assembly of claim 13, wherein the bone engagement member guide defines a transverse locking hole, the breakaway stud defines a corresponding transverse locking hole, and the locking holes are configured to receive a locking mechanism such that the bone engagement member guide and the intramedullary device are removably attached together by the locking mechanism.

16. The intramedullary device assembly of claim 13, wherein the intramedullary device defines a nub having a circumferential lip configured to at least partially engage the bone engagement member guide.

17. The intramedullary device assembly of claim 1, wherein the intramedullary device defines a plurality of holes to accept a plurality of fasteners for securing the bone to the intramedullary device.

18. The intramedullary device of claim 17 wherein at least one of the plurality of holes is configured to have a chamfered opening to accept at least one of the respective plurality of fasteners.

19. An intramedullary device assembly for repairing a defect of a bone, the assembly comprising:
    an intramedullary device configured to be inserted into a medullary canal of the bone and secured to the bone on either side of the defect;
    a bone engagement member guide removably attached to an end of the intramedullary device; and
    a bone engagement member comprising a plurality of discrete pressing elements configured to engage an end of the bone, wherein the bone engagement member is at least partially disposed within, and movable along, the bone engagement member guide, wherein application of force on the bone engagement member in the direction of the bone advances the bone engagement member along the bone engagement member guide towards the intramedullary device and allows at least one of the pressing elements to engage the end of the bone.

20. The intramedullary device assembly of claim 19, wherein the bone engagement member guide includes a tab configured to fit in a corresponding notch in the intramedullary device to limit rotation of the bone engagement member guide with respect to the intramedullary device.

21. The intramedullary device assembly of claim 19, wherein the intramedullary device includes a tab configured to fit in a corresponding notch in the bone engagement guide member to limit rotation of the bone engagement member guide with respect to the intramedullary device.

22. The intramedullary device assembly of claim 19 further comprising a breakaway stud connecting the intramedullary device and the bone engagement member guide, wherein the breakaway stud is configured to break when a predetermined amount of force is applied to the intramedullary device assembly such that the breakaway stud can be removed from the intramedullary device.

23. The intramedullary device assembly of claim 22, wherein the bone engagement member guide defines a transverse locking hole, the breakaway stud defines a corresponding transverse locking hole, and the locking holes are configured to receive a locking mechanism such that the bone engagement member guide and the intramedullary device are removably attached together by the locking mechanism.

24. The intramedullary device assembly of claim 22, wherein the intramedullary device defines a nub having a circumferential lip configured to at least partially engage the bone engagement member guide.

25. The intramedullary device assembly of claim 24, wherein the nub is initially positioned within the bone engagement member guide, and wherein an outer surface of the bone engagement member guide defines an indicator to indicate the position of the nub within the bone engagement member guide.

26. A guide adapter for attaching a compression member and drill guide to an intramedullary device comprising:
    a bone engagement member guide, wherein one end of the bone engagement member guide is configured to engage the intramedullary device and limit rotation of the bone engagement member guide with respect to the intramedullary device, and another end of the bone engagement member guide is configured to support the compression member; and a bone engagement member that is disposed at least partially within, and movable along, the bone engagement member guide, wherein the bone engagement member defines at least two bone engagement points and wherein at least one bone engagement point is movable relative to at least one other bone engagement point and is configured to engage an end of a bone when the intramedullary device is installed.

27. The guide adapter of claim 26, wherein the bone engagement member guide defines an elongated void, and wherein the bone engagement member includes an internal part configured to be movably retained within the elongated void of the bone engagement member guide and an external part configured to extend outside of the elongated void of the bone engagement member guide and engage the end of the bone via the at least two bone engagement points.

28. The guide adapter of claim 27, wherein the external part of the bone engagement member comprises a plurality of pressing elements configured to engage the end of the bone, and at least one of the pressing elements is shorter than at least one other pressing element.

29. The guide adapter of claim 26, wherein the bone engagement member guide defines a keyway slot configured to permit alignment of the drill guide with respect to the guide adapter when the drill guide is attached to the guide adapter.

30. The guide adapter of claim 26, wherein one end of the guide adapter is configured to attach to a breakaway stud connecting the guide adapter to the intramedullary device.

31. A method of assembling an intramedullary device assembly for repairing a defect of a bone comprising:

attaching a guide adapter to a proximal end of an intramedullary device, wherein the guide adapter comprises:

a bone engagement member guide having a first end configured to attach to the proximal end of the intramedullary device; and a bone engagement member that is at least partially disposed within, and movable along, the bone engagement member guide, wherein the bone engagement member defines at least two bone engagement points and wherein at least one bone engagement point is movable relative to at least one other engagement point in the direction of the bone; and attaching a compression member to a second end of the bone engagement member guide such that the compression member is movable along an axis of the bone engagement member guide.

32. The method of claim 31 further comprising attaching a drill guide to the guide adapter, wherein the drill guide is configured to allow drilling holes through the bone that are in alignment with corresponding holes defined by the intramedullary device.

33. The method of claim 32 wherein a cannula is configured to engage the drill guide to aid precision of placement and depth of the holes to be drilled.

34. The method of claim 32 wherein an external rotation guide is configured to allow proper alignment of the drill guide and the bone.

35. The method of claim 31, wherein attaching the guide adapter to the proximal end of the intramedullary device comprises attaching a breakaway stud to the proximal end of the device and attaching the first end of the bone engagement member guide to the breakaway stud.

36. The method of claim 35, wherein attaching the guide adapter to the proximal end of the intramedullary device further comprises engaging the guide adapter with a lip formed on a nub defined by the proximal end of the intramedullary device.

37. The method of claim 35, wherein attaching the guide adapter to the proximal end of the intramedullary device further comprises inserting a locking mechanism through corresponding transverse locking holes formed in the guide adapter and the breakaway stud.

38. A method of applying compression to repair a defect of a bone using an intramedullary device assembly including an intramedullary device, a bone engagement member guide attached to the intramedullary device, a bone engagement member disposed at least partially within the bone engagement member guide and defining at least two bone engagement points for engaging the bone, the method comprising:

inserting the intramedullary device of the intramedullary device assembly into a medullary canal of the bone;

securing the intramedullary device to a distal segment of the bone located on a distal side of the defect;

permitting movement of at least one bone engagement point of the bone engagement member relative to at least one other bone engagement point in the direction of a proximal segment of the bone;

advancing the distal and proximal bone segments towards each other by applying compression to the bone engagement member such that the proximal segment of the bone is moved towards the distal segment of the bone; and securing the intramedullary device to the proximal segment of the bone to maintain the positions of the distal and proximal segments of the bone.

39. The method of claim 38 further comprising detaching the bone engagement member guide from the intramedullary device after the proximal segment of the bone has been secured.

40. The method of claim 39 further comprising applying force to a breakaway stud attached to the proximal end of the intramedullary device in order to separate the breakaway stud from the intramedullary device.

* * * * *